(12) United States Patent
Kilbey et al.

(10) Patent No.: US 11,432,954 B2
(45) Date of Patent: Sep. 6, 2022

(54) INFLATABLE FLEXION-CORRECTING KNEE BRACE

(71) Applicants: Bryan E. Kilbey, DeFunaik Spring, FL (US); Nikhil N. Verma, Chicago, IL (US); Alan Getgood, London (CA); Tad L. Gerlinger, Chicago, IL (US)

(72) Inventors: Bryan E. Kilbey, DeFunaik Spring, FL (US); Nikhil N. Verma, Chicago, IL (US); Alan Getgood, London (CA); Tad L. Gerlinger, Chicago, IL (US)

( * ) Notice: Subject to any disclaimer, the term of this patent is extended or adjusted under 35 U.S.C. 154(b) by 545 days.

(21) Appl. No.: 16/427,457

(22) Filed: May 31, 2019

(65) Prior Publication Data

US 2020/0375772 A1 Dec. 3, 2020

(51) Int. Cl.
*A61F 5/03* (2006.01)
*A61F 5/01* (2006.01)
*A61F 13/06* (2006.01)

(52) U.S. Cl.
CPC ............ *A61F 5/012* (2013.01); *A61F 5/0106* (2013.01); *A61F 13/061* (2013.01)

(58) Field of Classification Search
CPC ...... A61F 5/012; A61F 5/0106; A61F 13/061; A61F 5/0111; A61F 5/00; A61F 5/0123; A61F 5/0102; A61F 5/01; A61F 5/0104
See application file for complete search history.

(56) References Cited

U.S. PATENT DOCUMENTS 10,092,438 B2 * 10/2018 Salsbery ................. A61F 5/012
2011/0207585 A1 * 8/2011 Burns ................ A63B 21/0004
482/124

* cited by examiner

*Primary Examiner* — Tarla R Patel
(74) *Attorney, Agent, or Firm* — J. Wiley Horton

(57) ABSTRACT

A knee brace with an inflatable air bladder. In a post-surgical embodiment the brace includes a rigid shell that fits behind the knee. The rigid shell includes an inflatable air bladder on its posterior surface. A wrap is placed around the knee and the air bladder. When the air bladder is inflated, the knee is urged in the posterior direction—thereby decreasing flexion. In a rehabilitative embodiment, a rigid shell is placed over the anterior portion of the knee. An air bladder is positioned between the rigid shell and the knee. The rigid shell is held in place using the securing straps of the rehabilitative brace. When the air bladder is inflated the knee is again urged in the posterior direction.

20 Claims, 26 Drawing Sheets

INFLATABLE FLEXION-CORRECTING KNEE BRACE

BACKGROUND OF THE INVENTION

1. Field of the Invention

This invention relates to the field of medical products. More specifically, the invention comprises a knee brace that is configured to establish and maintain a zero-degree flexion state (full extension or hyper-extension) for the human knee.

2. Description of the Related Art

Brace hardware is used for many purposes on the human knee. A first example is an immobilizing brace used after knee surgery. A second example is during rehabilitative treatment where a stabilizing brace is needed while the knee is moved through a desired range of motion. In most all cases the regulation of knee flexion is a significant concern.

FIG. 1 provides a simple illustration of the flexion and extension motions of the human knee. Thigh 12 is held stationary and lower leg 14 is pivoted about knee 10. Extension in this context means aligning the lower leg with the thigh, while flexion means bending the knee so that the lower leg assumes the position shown by the dashed line in FIG. 1.

FIG. 2 illustrates the frame of reference that is generally used to measure knee flexion. Femur reference line 16 and tibia reference line 18 intersect at knee joint 20. When tibia reference line 18 is perfectly aligned with femur reference line 16 then a condition of 0° flexion exists (which is more commonly referred to as a condition of full extension). The full range of motion—which varies from patient to patient—is represented by about 135° of flexion.

Following surgery it is often desirable to place the knee joint in a normal state of full extension. For some patients a fully extended state is a true 0° flexion/full extension state. In other cases a patient's normal state is an extension beyond 0° (mild hyper-extension). Prior art devices have difficulty placing the knee in this range of 0° flexion to mild hyper-extension. FIG. 3 shows a prior art post-surgical brace. Rigid shell 21 is generally a foam-lined structure that is contoured to fit the back of the leg from the middle of the calf up through the middle of the thigh. Four adjustable straps are used to tighten the fit of the shell to the leg. These are: thigh strap 22, superior knee strap 24, inferior knee strap 26, and shin strap 28.

The four straps are selectively tightened to align the leg with the splint. In most cases, however, such splints only achieve a minimum flexion of about 5°. The compliance of the leg's soft tissues inhibits the achievement of a true 0° of flexion. It is preferable to provide a solution that can accommodate variations in anatomy and gradually increase the force used to reduce knee flexion.

FIG. 12 shows another type of prior art knee brace—rehabilitation brace 76. This type of brace includes a rigid hinge assembly on each side of the knee. Only the inside hinge assembly is shown in FIG. 12. The outside hinge assembly is typically a mirror image of the inside hinge assembly, however. Adjustable pivot joint 78 is located as close as practical to the knee's pivoting axis. Superior strut 80 extends upward from the adjustable pivot joint while inferior strut 84 extends downward.

Adjustable pivot joint 78 is "adjustable" in that it includes a pair of stops that can be used to select desired limits for flexion and extension. Generally the adjustable stops will limit the range of motion for flexion and extension. These stops are often moved as the rehabilitation progresses. However, it is significant to note that even when the minimum flexion is set to 0° the brace cannot effectively force the knee joint to actually assume 0° of flexion. This is once again the result of the pliable nature of the leg tissues, and the variability in the application of the brace.

The rigid struts 80, 84 are connected to the leg via encircling cuffs and straps. For example, thigh cuff 86 is an open loop that encircles the user's upper thigh. Thigh strap 88 passes around the cuff. It has an adjustable length so that it can be adjusted to a desired tension. Superior knee cuff 90 encircles the thigh just above the knee. This cuff is tightened using superior knee strap 92.

Inferior knee cuff 94 encircles the upper calf. This cuff is tightened using inferior knee strap 96. Shin cuff 98 encircles the lower leg and is tightened using shin strap 100. The physician can set adjustable pivot joint 78 to 0° of flexion (some can even be set to a slightly negative value—such as –5° of flexion). Many such prior art braces do not include the cuffs and only use the straps to secure to struts to the leg. An invention intended for use with such prior art braces is preferably configured to work with or without cuffs.

A solution that can accommodate variations in anatomy and gradually increase the force used to reduce knee flexion is needed. The present invention provides such a device.

BRIEF SUMMARY OF THE PRESENT INVENTION

The present invention comprises a knee brace with an inflatable air bladder. In a post-surgical embodiment the brace includes a rigid shell that fits behind the knee. The rigid shell includes an inflatable air bladder on its posterior surface. A wrap is placed around the knee and the air bladder. When the air bladder is inflated, the knee is urged in the posterior direction—thereby decreasing flexion. In a rehabilitative embodiment, a rigid shell is placed over the anterior portion of the knee. An air bladder is positioned between the rigid shell and the knee. The rigid shell is held in place using the securing straps of the rehabilitative brace. When the air bladder is inflated the knee is again urged in the posterior direction.

Figure 1:
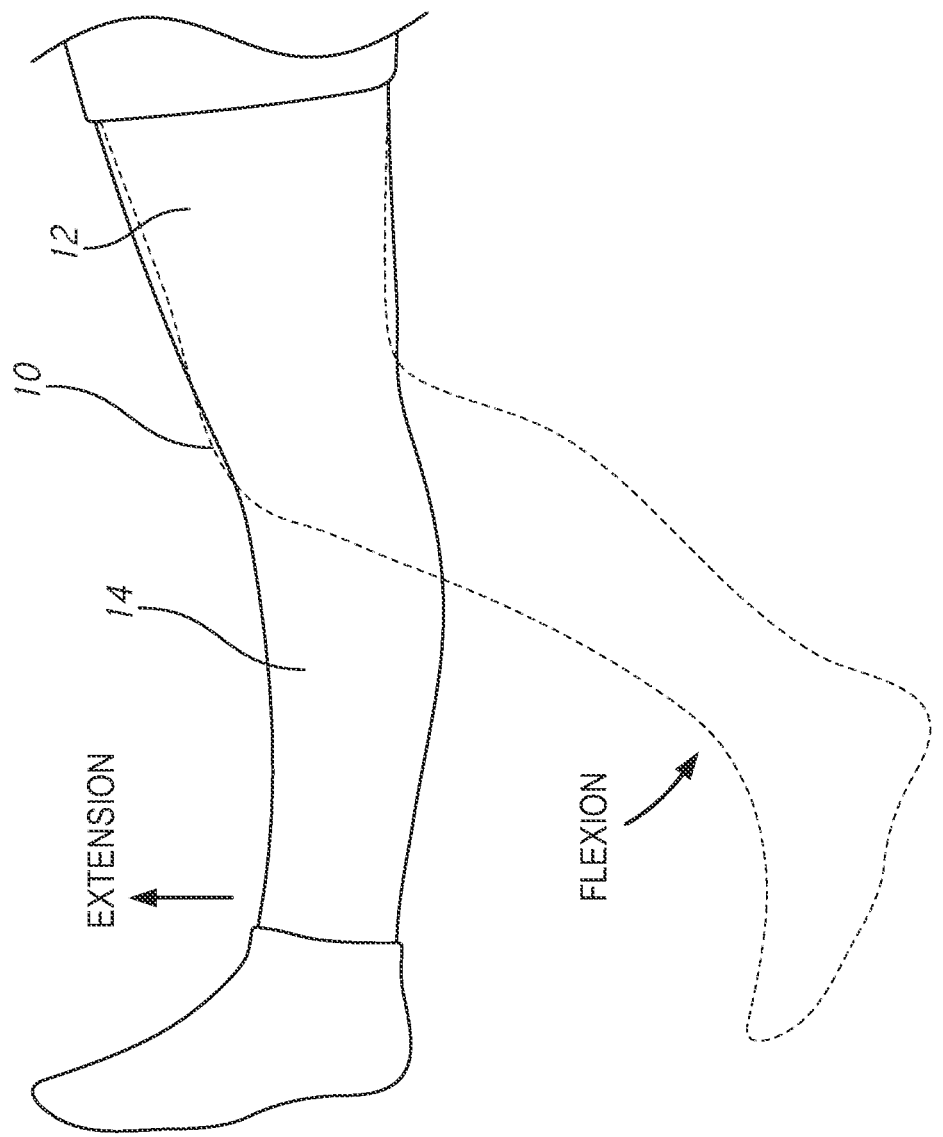
FIG. 1 is an elevation view, showing flexion and extension of the human knee.
Figure 2:
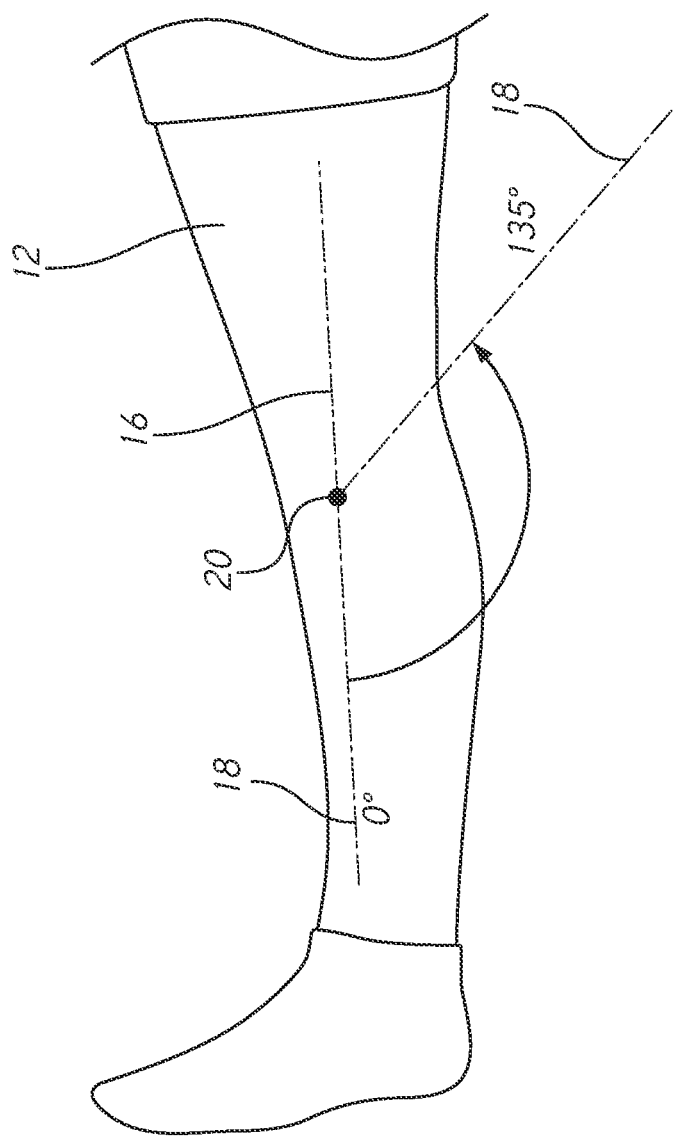
FIG. 2 is an elevation view, showing the conventional frame of reference for measuring knee flexion.
Figure 3:
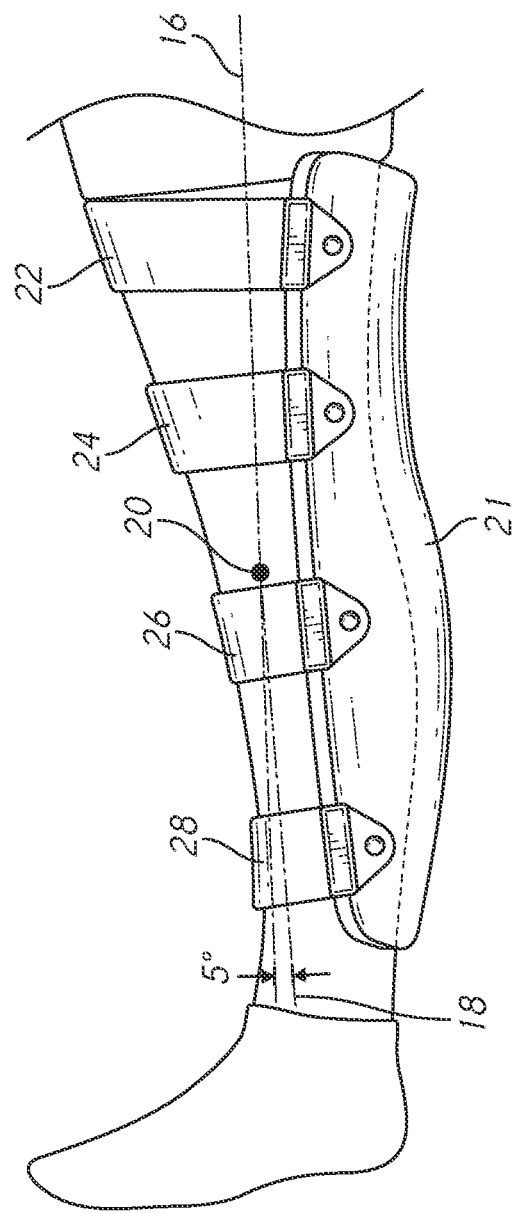
FIG. 3 is an elevation view, showing a prior art post-operative splint that is designed to limit knee flexion.
Figure 4:
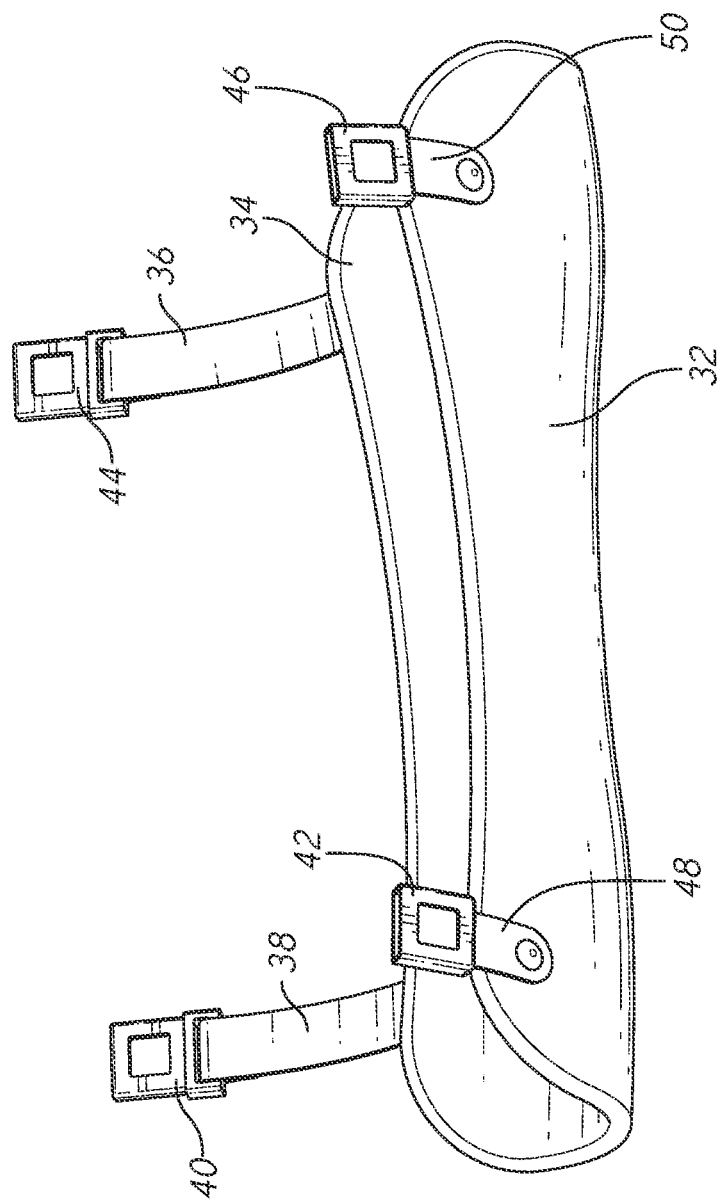
FIG. 4 is a perspective view, showing some of the components of an embodiment of the present invention.

REFERENCE NUMERALS IN THE DRAWINGS 10 knee
12 thigh
14 lower leg
16 femur reference line
18 tibia reference line
20 knee joint
21 rigid shell
22 thigh strap
24 superior knee strap
26 inferior knee strap
28 shin strap
30 splint chassis
32 rigid shell
34 pliable liner
36 thigh strap
38 shin strap
40 male snap buckle
42 female snap buckle
44 male snap buckle
46 female snap buckle
48 pivot strap
50 pivot strap
52 bladder housing
54 squeeze bulb
56 air line
58 valve
60 knee wrap
62 knee cap relief
64 pull tab
65 first lateral edge
66 exterior surface
68 interior surface
70 hook panel
72 air bladder
74 air volume
76 rehabilitation brace
78 adjustable pivot joint
80 superior strut
84 inferior strut
86 thigh cuff
88 thigh strap
90 superior knee cuff
92 superior knee strap
94 inferior knee cuff
96 inferior knee strap
98 shin cuff
100 shin strap
102 rigid shell
104 flexion correcting brace
106 superior knee cover
108 inferior knee cover
110 knee dome
112 lateral relief
114 perimeter
116 staked seam
118 inner perimeter
120 inflatable bladder
121 splint chassis
122 pliable liner
124 alignment marks
126 thigh strap
128 shin strap
130 knee strap
132 hook panel
134 pull tab
136 patella slit
138 male snap buckle
140 female snap buckle
142 male snap buckle
144 female snap buckle
146 rigid shell
148 lateral relief
150 integrated bladder
152 loop panel
154 cold pack
160 air bladder

DETAILED DESCRIPTION OF THE INVENTION

FIGS. 4-11 illustrate a first embodiment of the invention that is configured for use as a post-operative brace for reconstructive knee procedures such as ligament reconstruction and total knee replacements (though it may have many other applications as well). Rigid shell 32 is thin-walled contoured structure intended to rest against the back of the leg. It may be made of metal—such as soft aluminum. It may also be made of molded composite materials. An outer coating may be provided (such as a soft spray coating or a fabric layer that is glued in place).

Pliable liner 34 is provided on the side facing the patient's leg. A sot foam may be used in this layer—with a fabric covering. Many other materials may be substituted. Shin strap 38 is secured to the far side of the rigid shell (not shown). The distal end of the strap includes male snap buckle 40. Female snap buckle 42 is secured to the near side of the shell via pivot strap 48. The user mates snap buckles 40, 42 to secure shin strap 38 in place. A length adjustment is provided in the strap so that the tension can be adjusted.

Thigh strap 36 includes male snap buckle 44. Female snap buckle 46 is connected to the shell via pivot strap 50. The thigh strap is secured by connecting the two snap buckles 44, 46. A length adjustment is provided for this thigh strap as well.

Figure 5:
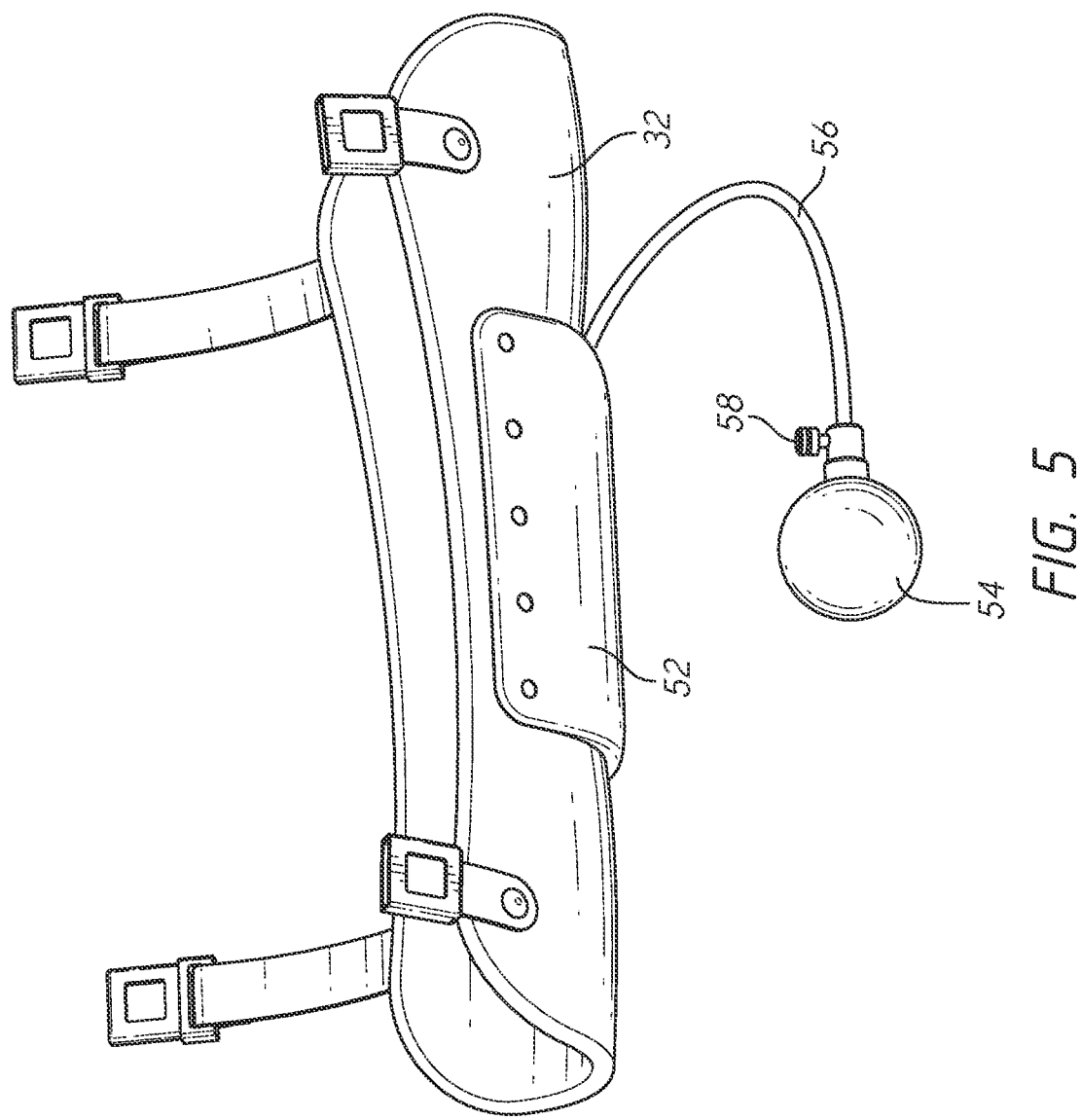
FIG. 5 is a perspective view, showing some of the components of an embodiment of the present invention.

FIG. 5 shows the shell assembly with the addition of bladder housing 52. The bladder housing encloses an inflatable air bladder. Air line 56 leads from this inflatable air bladder to squeeze bulb 54 and valve 58. Squeezing and releasing the squeeze bulb gradually inflates the air bladder within bladder housing 52. Actuating valve 58 releases the accumulated air pressure and deflates the air bladder.

Figure 6:
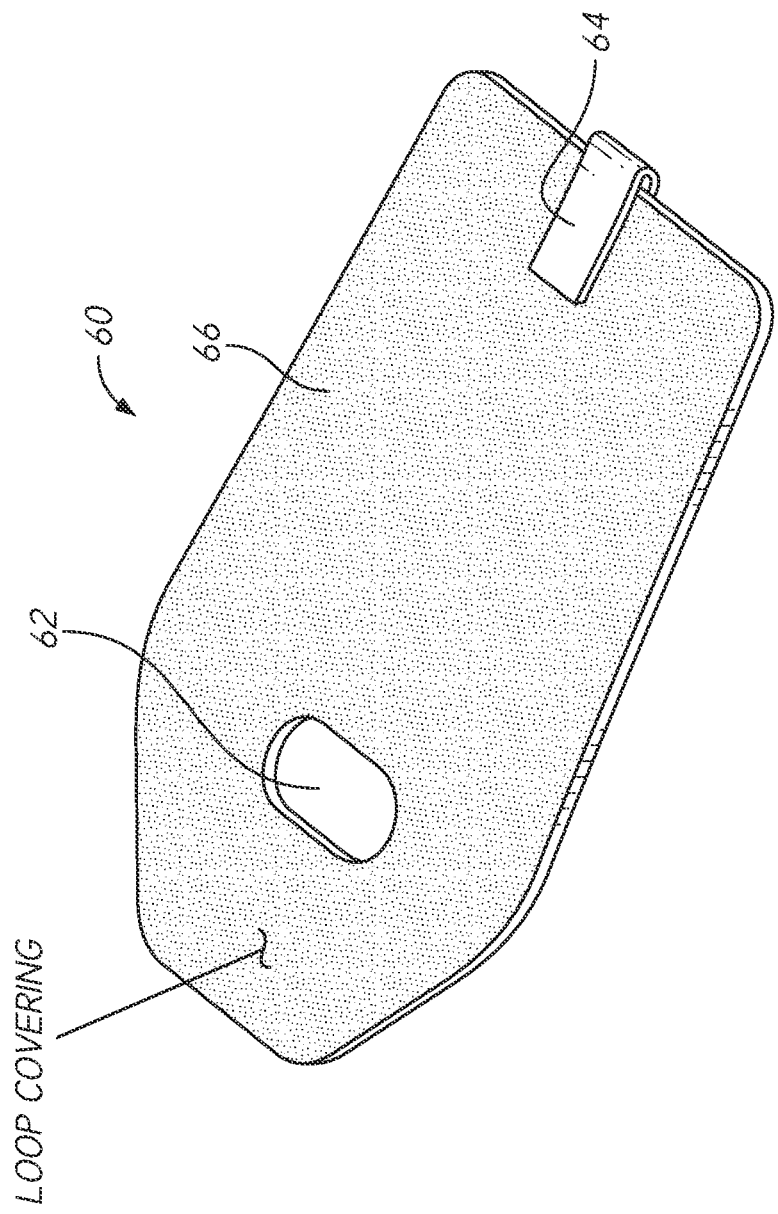
FIG. 6 is a perspective view, showing the knee wrap used in the present invention.

FIG. 6 shows a second significant component of the embodiments of FIGS. 4-11. Knee wrap 60 is made of a soft material that does not stretch. Knee cap relief 62 is sized to fit over the patient's patella. Pull tab 64 is provided on one lateral side. Exterior surface 66 in this example is provided with a hook-compatible material. This is not necessarily a thick loop pile material. A smooth material that nevertheless firmly engages a hook panel is preferred. Such materials are now widely available.

Figure 7:
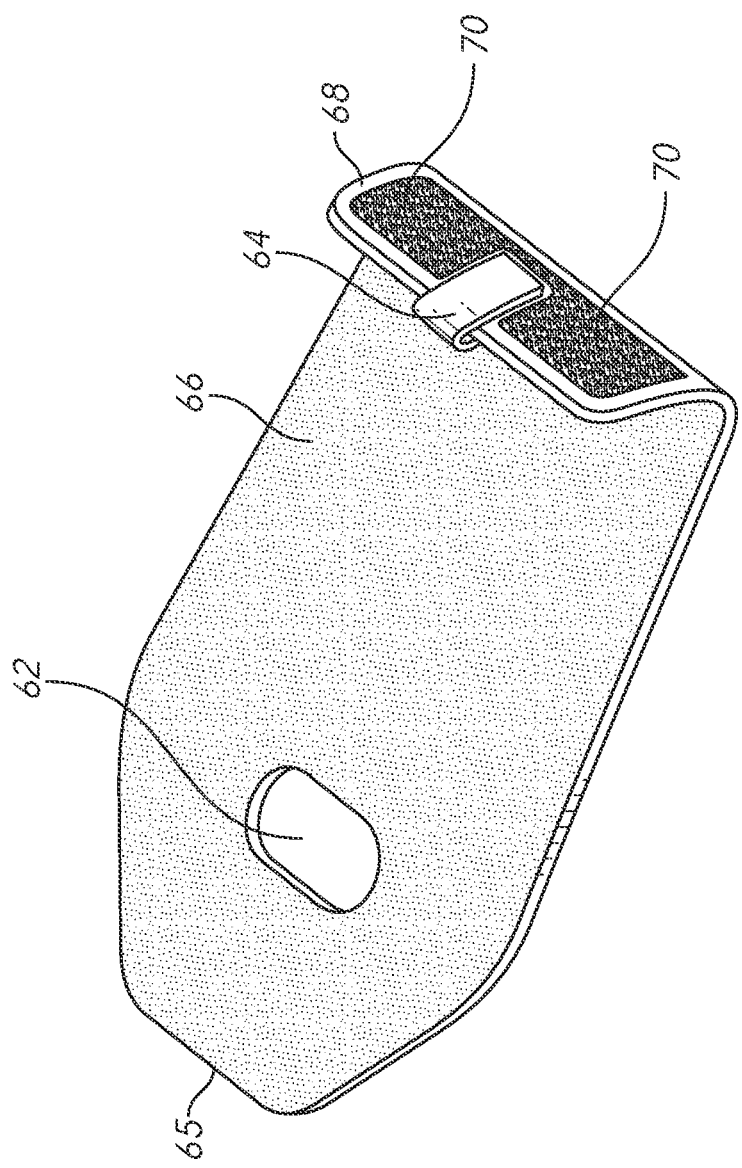
FIG. 7 is a perspective view, showing the knee wrap used in the present invention.

FIG. 7 shows the same knee wrap with one end turned upward to reveal interior surface 68. Hook panel 70 covers this interior surface proximate pull tab 64. The balance of the interior surface is covered in loop material. The knee wrap can be placed around the user's knee, then pulled to a desired tension and secured in position.

Figure 8:
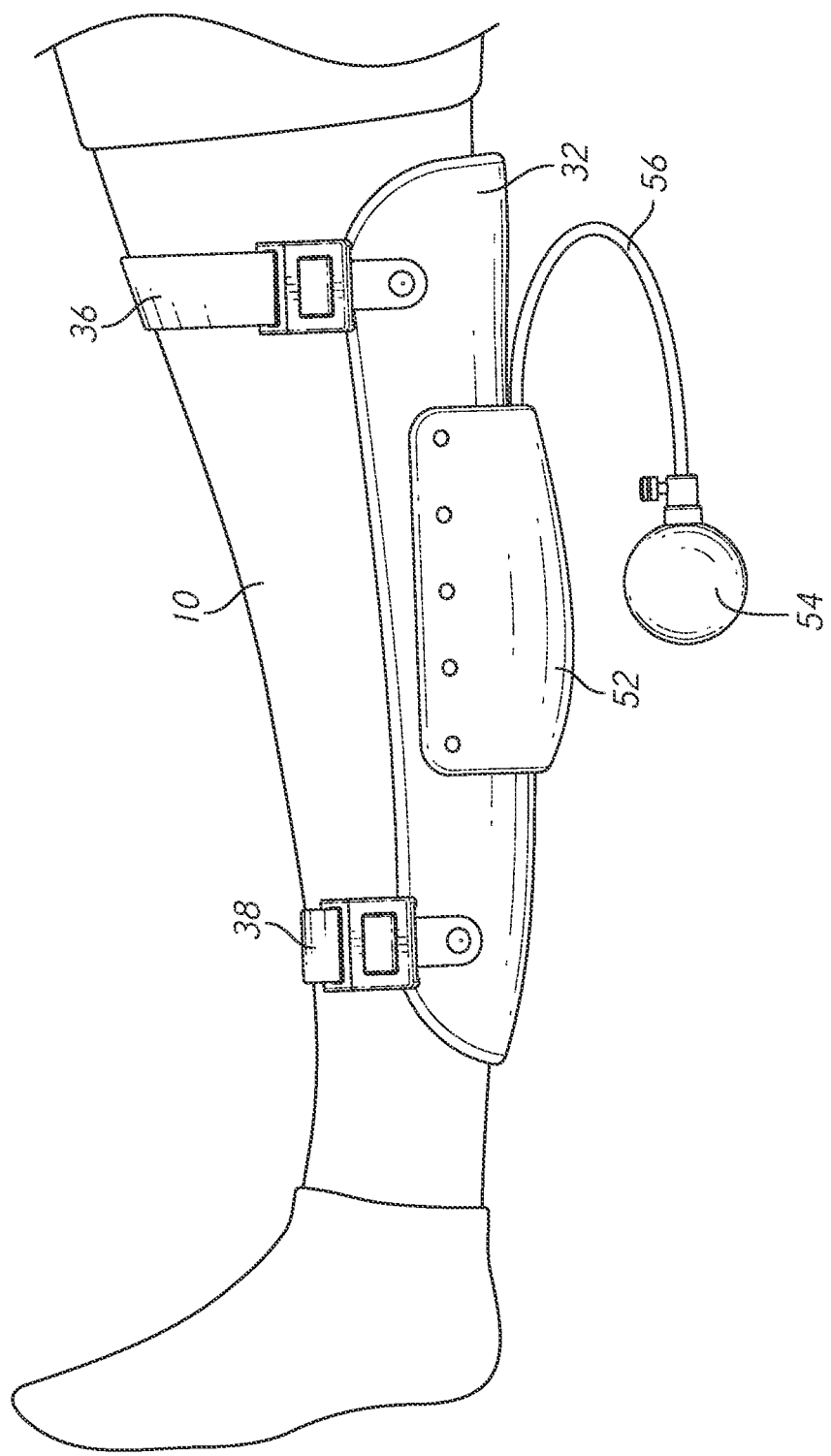
FIG. 8 is an elevation view, showing the installation of an embodiment of the present invention.

FIG. 8 shows the first step in the process of securing this embodiment of the inventive brace to a patient's leg. Rigid shell 32 is placed against the back of the leg and shin strap 38 and thigh strap 36 are secured and tightened to a desired degree.

Figure 9:
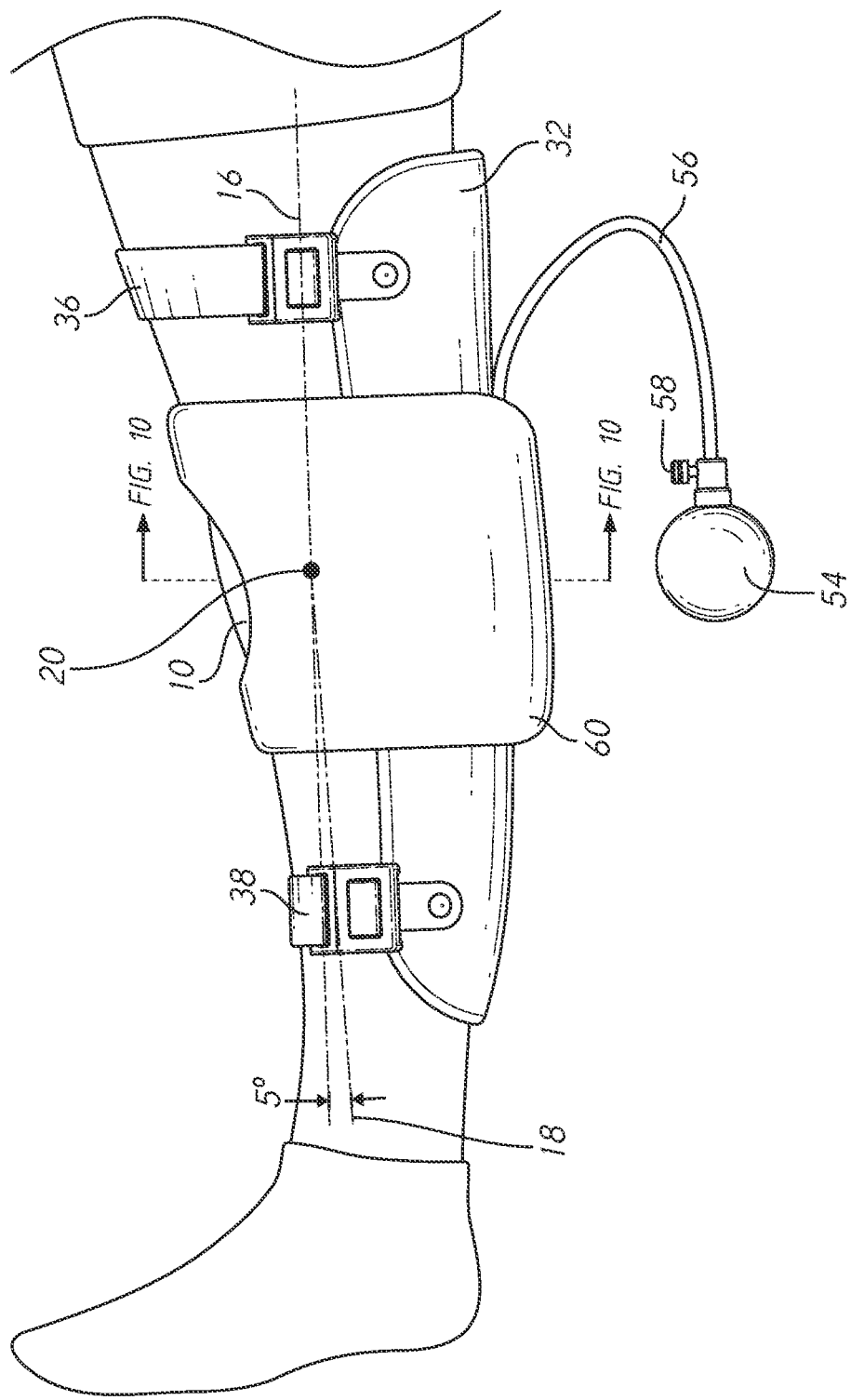
FIG. 9 is an elevation view, showing a completed installation of an embodiment of the present invention.

FIG. 9 shows the same assembly after knee wrap 60 has been secured in place. Returning briefly to FIG. 7, the knee wrap is positioned by placing knee cap relief 62 over the patient's knee cap. The user then pulls first lateral edge 65 down around the patient's leg. Pull tab 64 is used to tension the knee wrap to a desired degree. Once this desired level of tension is achieved, the user presses hook panels 70 against the wrap's exterior surface. The wrap is thereby secured in place as shown in FIG. 9.

In looking at tibia reference line 18 in FIG. 9, the user will note the presence of about 5° of knee flexion. This is a typical amount of flexion for a supposedly "straight" knee brace. However, in the embodiment of FIG. 9, the user can gradually reduce the amount of flexion by squeezing squeeze bulb 54. The inflation apparatus has the typical one-way valve so that the air bladder is inflated with each squeeze and only deflated by actuating valve 58. FIG. 9 has "call outs" indicating the section-view plane for FIG. 10.

Figure 10:
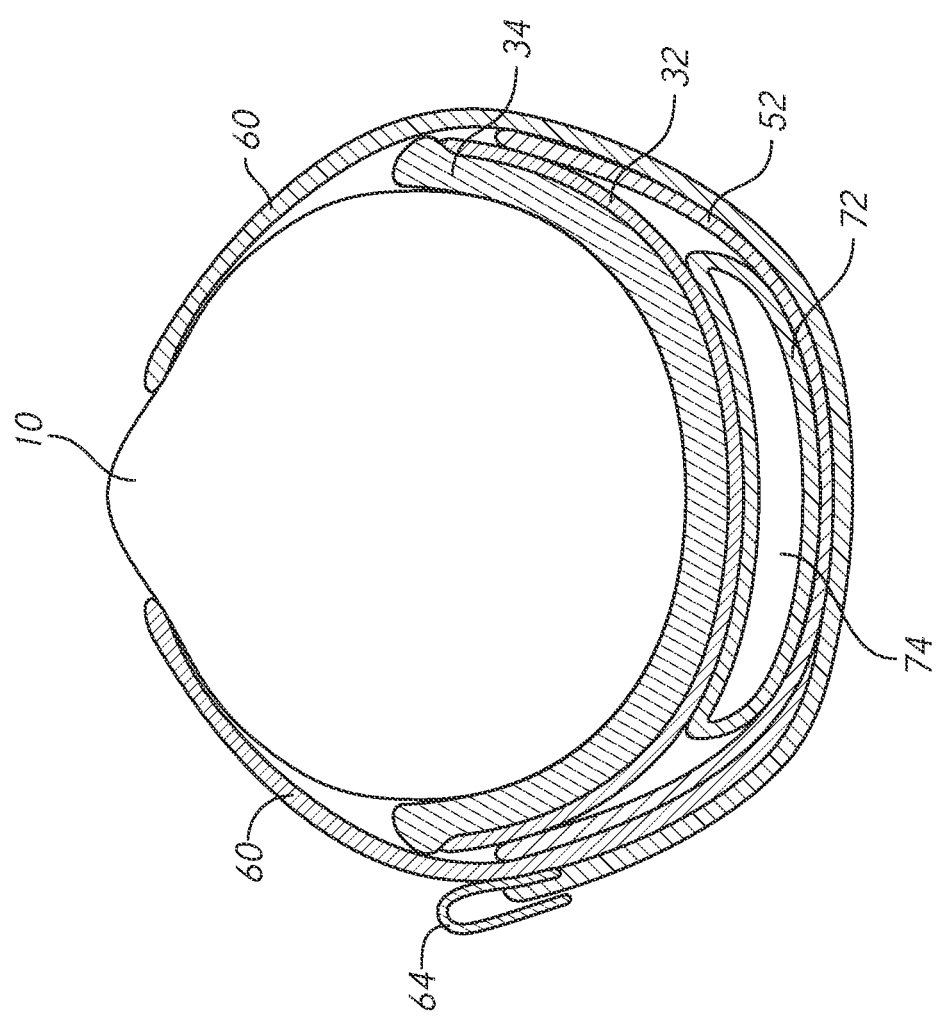
FIG. 10 is a sectional elevation view showing an embodiment of the present invention in an operational state.

FIG. 10 is a sectional elevation view that omits the internal details of the user's knee. Pliable liner surrounds the posterior section of the knee. As explained previously, the pliable liner is contained within rigid shell 32. Air bladder 72 is positioned on the posterior portion of the rigid shell and held in place by bladder housing 52. Knee wrap 60 encircles all these other constituents, with the knee relief being centered on knee 10. The reader will note how pull tab 64 has been used to adjust the tension and secure the knee wrap to itself. The knee wrap does not tend to migrate because of the fact that the knee cap relief encircles the patient's knee. FIG. 10 shows air bladder 72 in a partially inflated state. Air volume 74 is contained within the air bladder.

Figure 11:
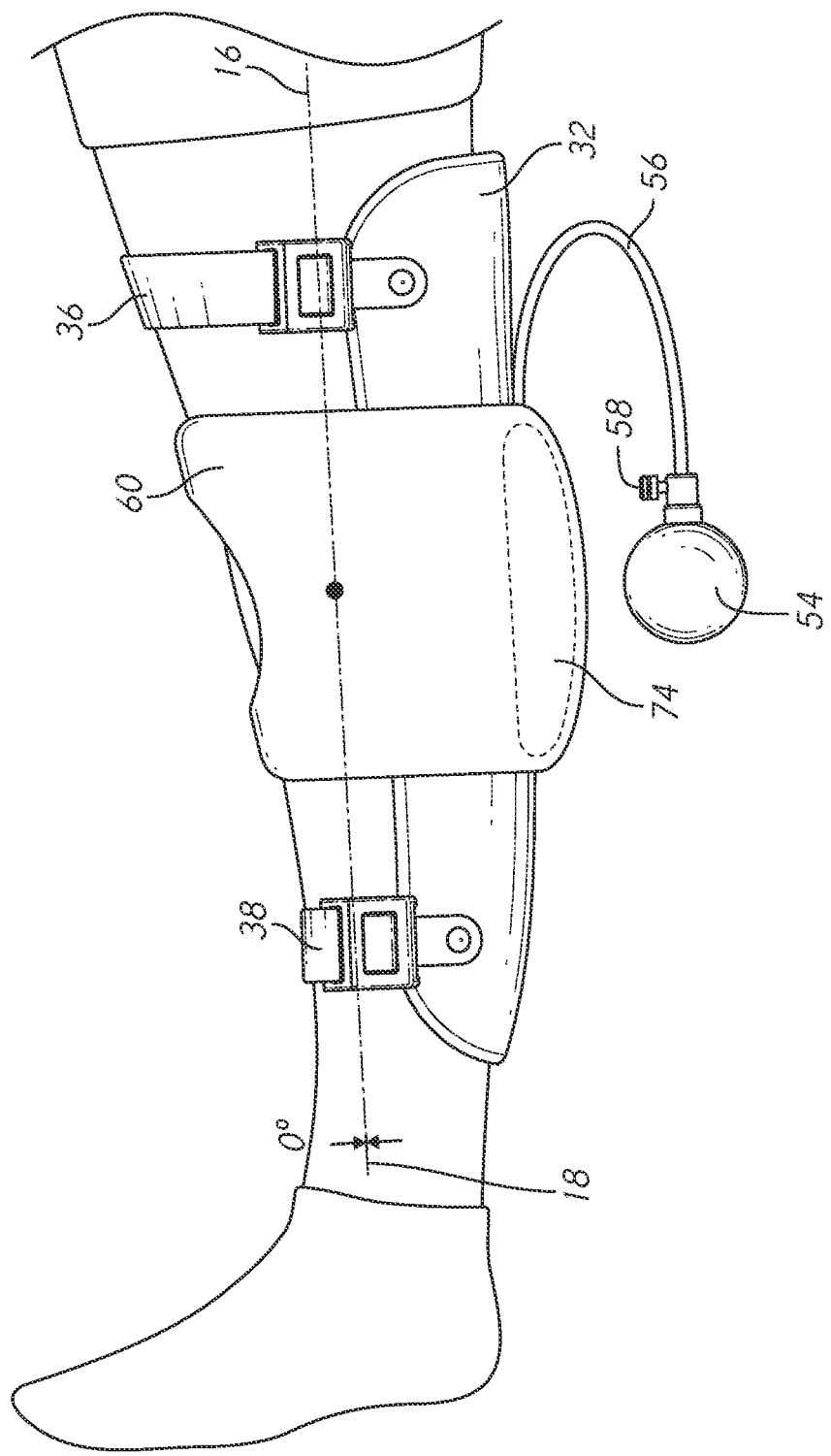
FIG. 11 is an elevation view showing an embodiment of the present invention in an operational state.

In FIG. 11 the air bladder has been inflated to a greater extent. In the context of the orientation shown in the view, the inflation of the air bladder (increase in air volume 74) causes knee wrap 60 to pull the knee further downward into the pliable liner within rigid shell 32 (pulls the knee in the posterior direction). There is no additional downward force with respect to thigh strap 36 or shin strap 38. Thus, the leg in the vicinity of straps 36, 38 remains in the same position while the leg in the vicinity of the knee joint is pulled downward (in a posterior direction). As the air volume increases the knee joint eventually reaches a true 0° flexion/full extension state.

Thus, the reader will understand that the embodiment of FIGS. 4-11 is able to place the knee joint in a true 0° flexion/full extension state. Further, the embodiment is adjustable over a moderate range of flexion near a true 0° flexion/full extension state.

Figure 12:
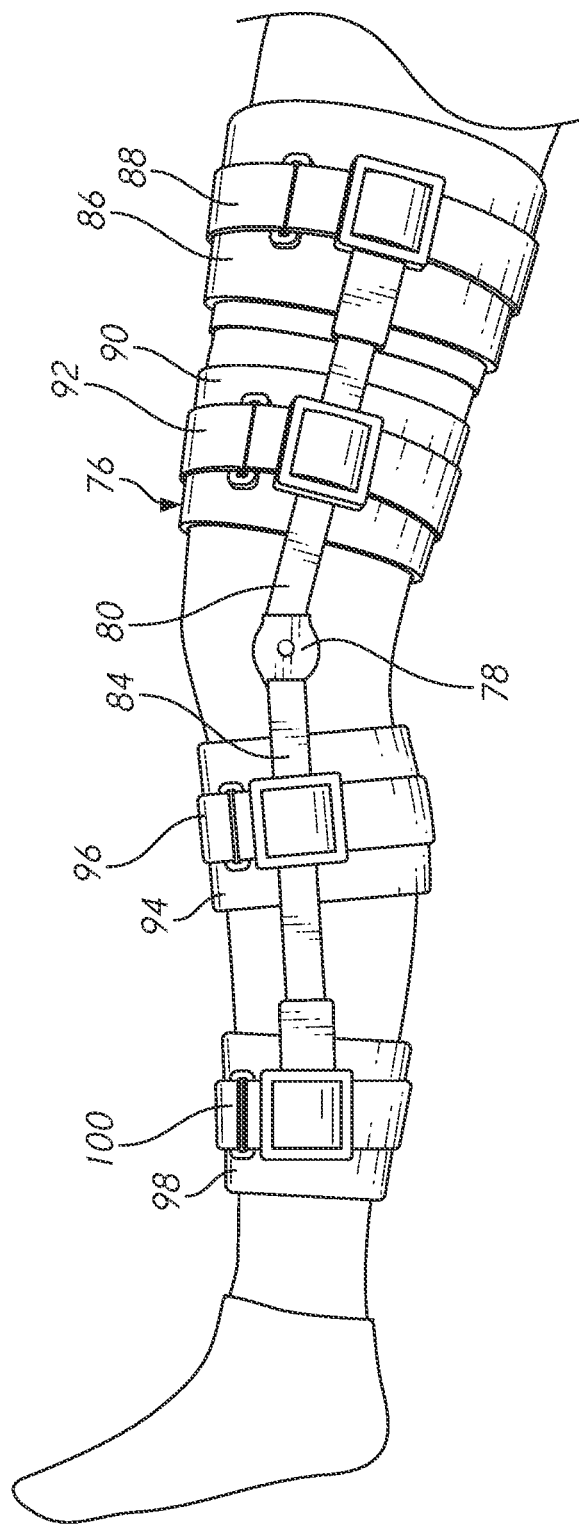
FIG. 12 is an elevation view, showing a prior art rehabilitation brace.

While the embodiment of FIGS. 4-11 is effective, it does not permit the knee to undergo significant flexion or range of motion while it is installed. In some situations a range of motion is desirable. Rehabilitation often requires an increasing range of motion. Rehabilitation braces such as shown in FIG. 12 are designed for these purposes. Such braces provide stability while allowing then knee joint to vary through a suitable range of motion. The embodiment of FIGS. 13-18 is configured to provide a true 0° flexion/full extension state or full extension state while also being compatible with a rehabilitation brace.

Figure 13:
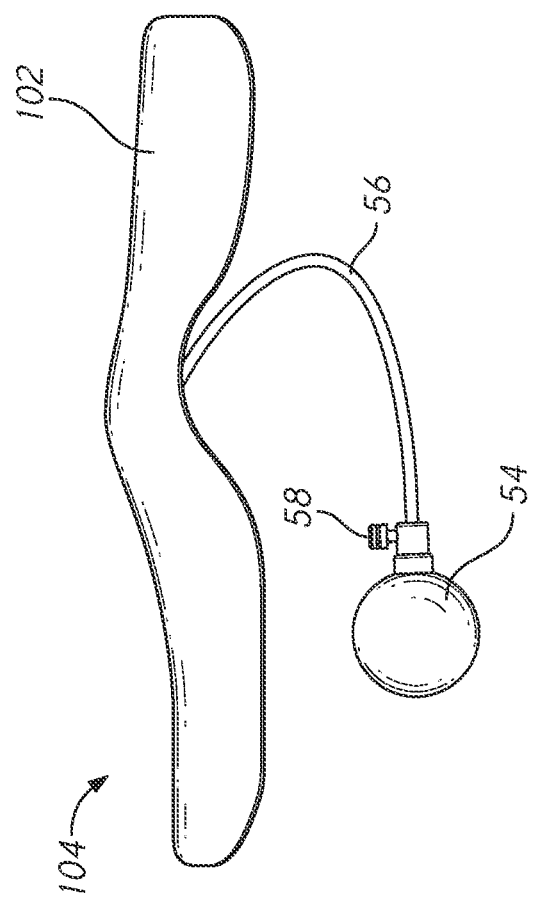
FIG. 13 is an elevation view, showing an embodiment of the present invention that is configured for use with a rehabilitation brace.

In looking at the prior art brace of FIG. 12, the reader will note that the anterior knee area is free of encumbrances. The embodiment of FIGS. 13-18 is intended to mount in this area. FIG. 13 shows a side view of flexion correcting brace 104. Rigid shell 102 is made of metal—such as soft aluminum. It may also be made of molded composite materials or other rigid materials. As the device will be in contact with the user a soft fabric covering is preferably provided.

An inflatable air bladder is contained within the rigid shell. As for the prior example, squeeze bulb 54 is used to selectively inflate the air bladder through air line 56. Valve 58 is used to selectively deflate the air bladder.

Figure 14:
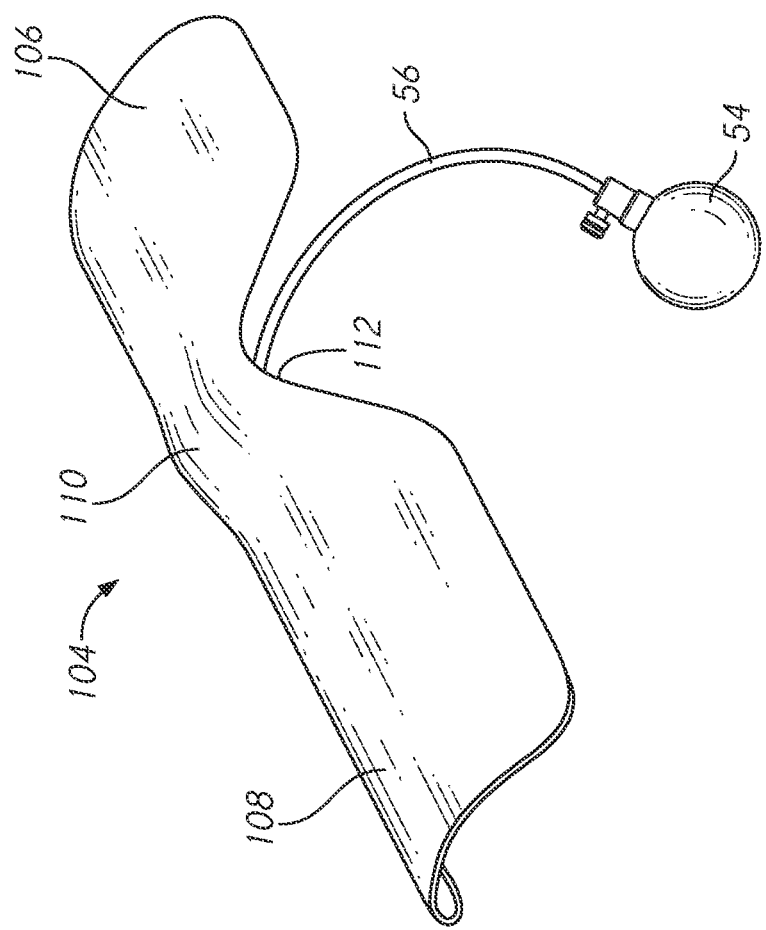
FIG. 14 is a perspective view, showing the embodiment of FIG. 13.

FIG. 14 provides a perspective view. The rigid shell includes superior knee cover 106 and inferior knee cover 108, joined by knee dome 110. The knee dome includes a raised region configured to fit comfortably over the patient's patella, thus eliminating any unwanted forces on the patella. A lateral relief 112 is provided on each side. These lateral reliefs provide clearance for the hinges found on prior art rehabilitation braces. Many physicians prefer to have no contact with the patella at all. It is thus desirable to provide some embodiments with a knee dome 110 that is much taller than the one shown in FIGS. 13-18.

Figure 15:
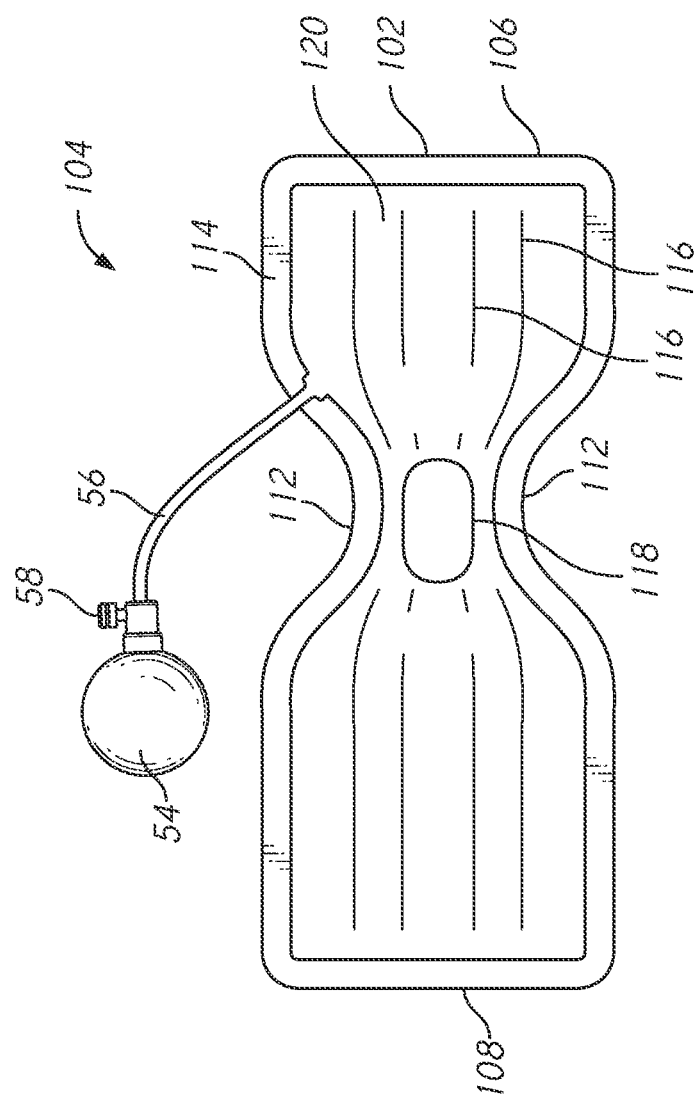
FIG. 15 is a bottom view, showing the embodiment of FIG. 13.

FIG. 15 provides a view of the opposite side of flexion correcting brace 104. In this view the reader is looking at the side of the device that faces the user's knee. Inflatable bladder 120 is contained under rigid shell 102. In the example shown the outer perimeter of the bladder is contained within the outer perimeter of the rigid shell. In other instances the bladder will have the same perimeter as the outer shell and in still other instances the bladder will extend out beyond the rigid shell. The posterior surface of the air bladder is optionally covered in a hook-compatible material so that a cold pack or hot packs can be stuck to the surface and pressed against the knee when the bladder is inflated.

In the example of FIG. 15, perimeter 114 defines the outer extent of the air bladder. The air bladder contains inner and outer walls that are sealed along perimeter 114. Several internal staked seams are also provided. The inner and outer walls of the air bladder are joined along these staked seams. The presence of the staked seams causes the air bladder to inflate in a series of tubular chambers that are analogous to the tubular chambers used on an air mattress. Some embodiments may include no staked seams at all, as the shape of the rigid shell, the shape of the knee, and the surrounding brace structure tend to contain the air bladder well without the need for shape-modifying staked seams.

An optional inner perimeter 118 is included in some embodiments. When present, this feature encircles the patient's patella. It helps to locate the air bladder in the desired location and eliminates unwanted pressure on the patella. As for the prior example, squeezing squeeze bulb 54 causes the air bladder to inflate and actuating valve 58 causes it to deflate.

Figure 16:
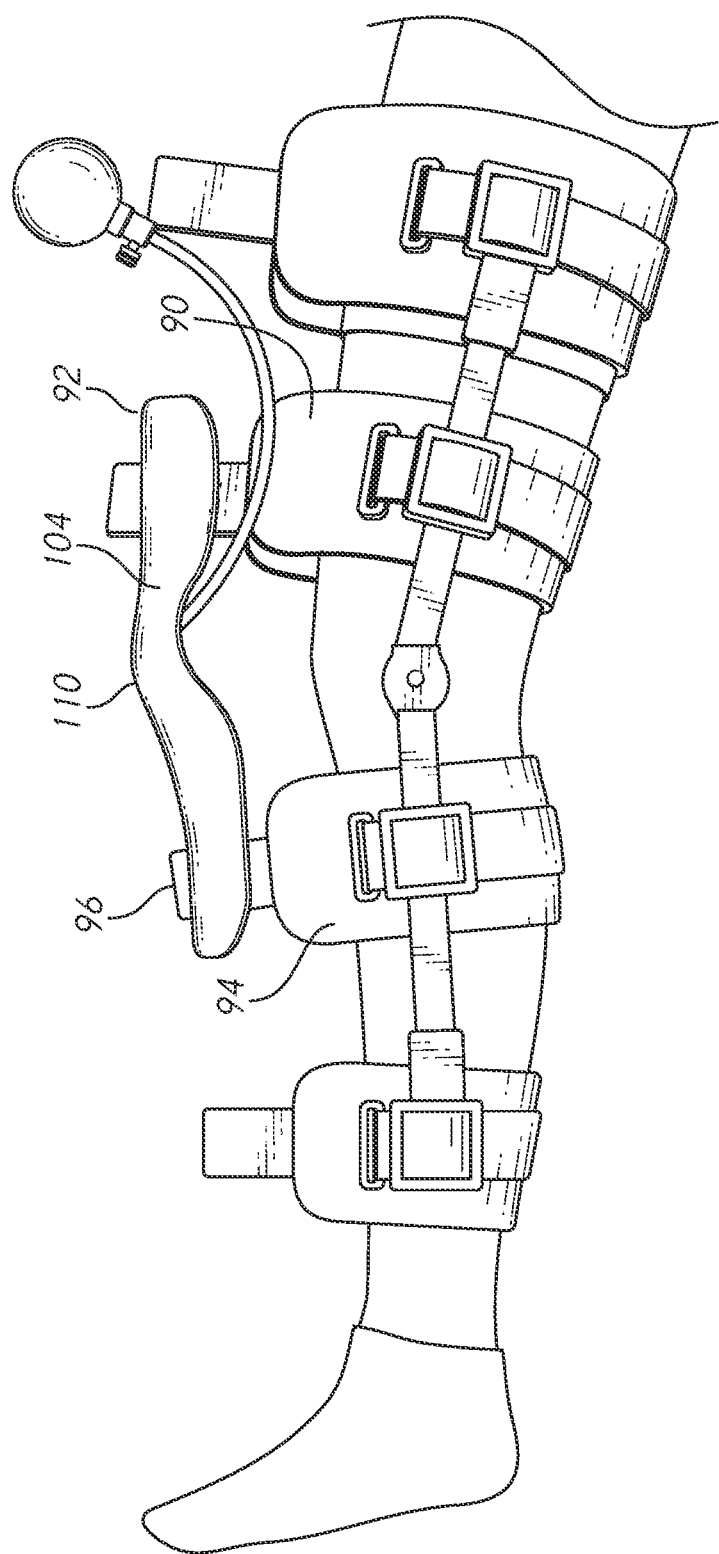
FIG. 16 is an elevation view, showing the embodiment of FIG. 13 being installed on a prior art rehabilitation brace.
Figure 17:
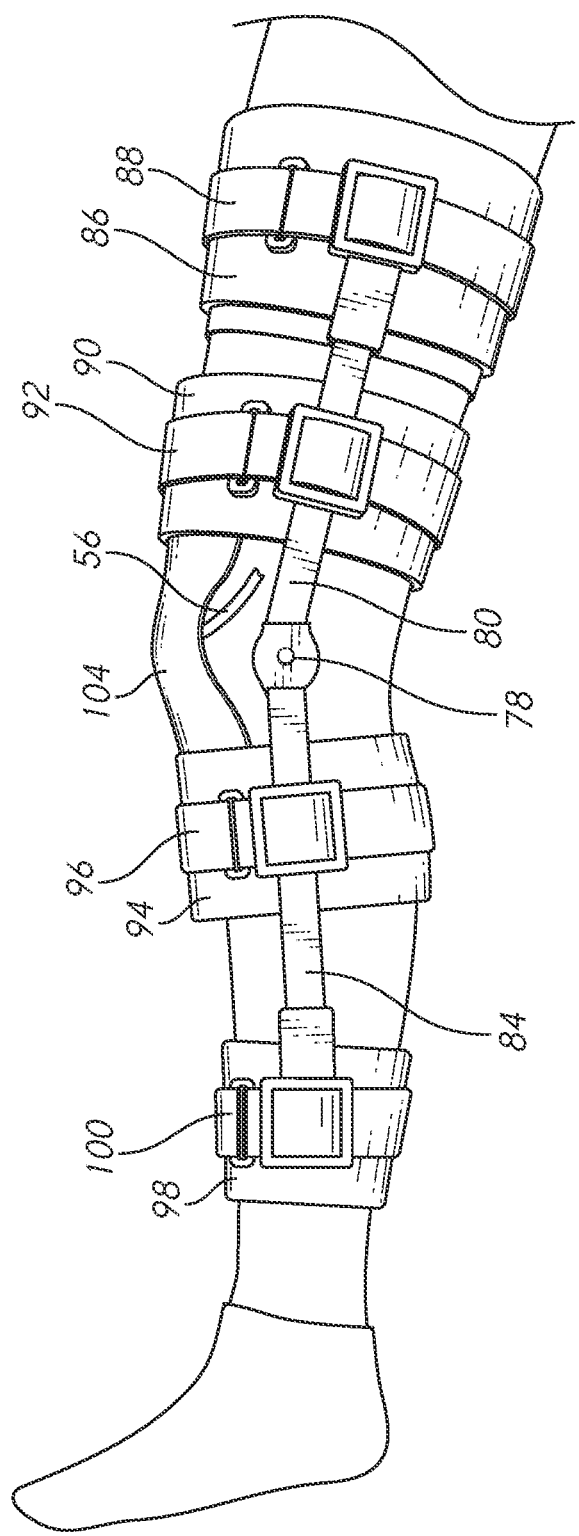
FIG. 17 is an elevation view, showing the embodiment of FIG. 13 being installed on a prior art rehabilitation brace.

FIGS. 16 and 17 show the process of installing this second embodiment. In FIG. 16, the encircling cuffs and straps have been opened. Although all the straps and cuffs are shown opened in this view, it is only generally necessary to open inferior knee strap 96 and superior knee strap 92. Cuffs 94,90 are opened to expose the anterior portions of the leg. Flexion correcting brace 104 is then lowered into position, with knee dome 110 resting over the patient's patella, FIG. 17 shows the assembly after inferior knee cuff 94, inferior knee strap 96, superior knee cuff 90, and superior knee strap 92 have all been closed over flexion correcting brace 104. The flexion correcting brace is thereby held in position. The collective assembly of flexion limiting brace 104 and the prior art rehabilitation brace 76 is referred to as a "flexion limiting knee brace assembly." Air line 56 is shown but the squeeze bulb has been omitted for purposes of visual clarity. The reader will note the angular relationship between superior strut 80 and inferior strut 84.

Figure 18:
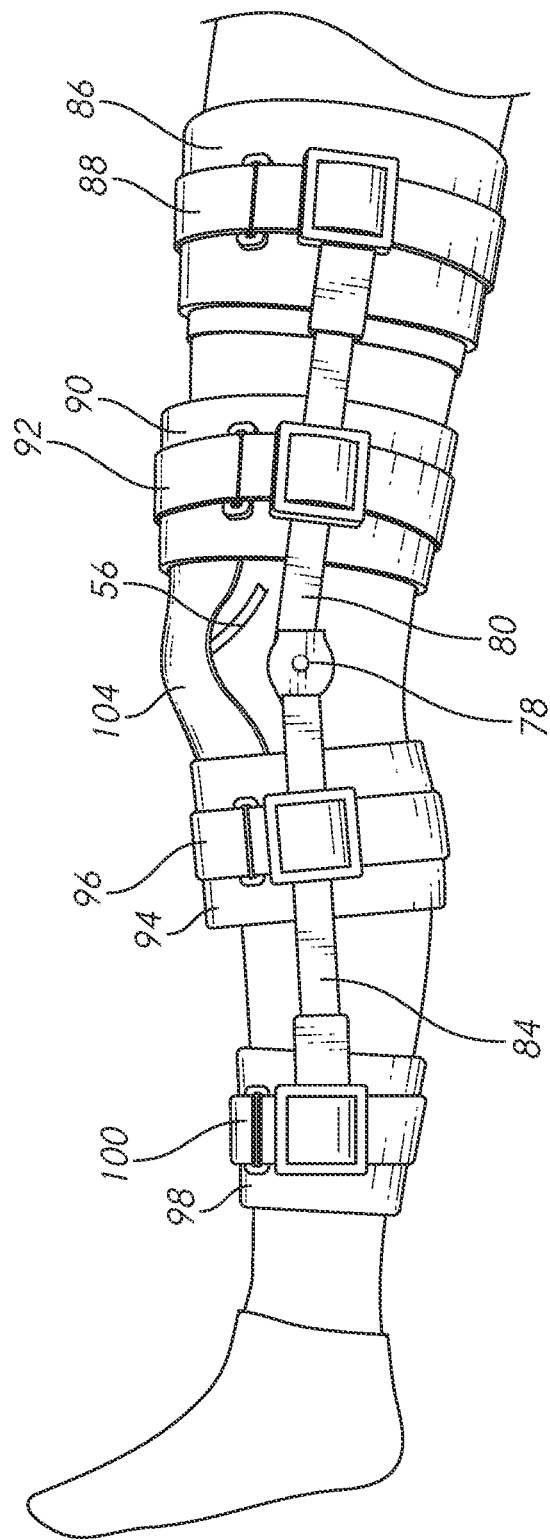
FIG. 18 is an elevation view, showing the actuation of the present invention with a prior art rehabilitation brace.

At this point the user begins inflating the air bladder within flexion correcting brace 104. The inflating air bladder pushes down on the anterior portion of the knee joint (urging the knee joint in the downward or posterior direction), FIG. 18 shows the same assembly after the air bag has been inflated to a considerable extent. The reader will note how inferior strut 84 is now aligned with superior strut 80 (The slight vertical offset is a common feature of adjustable pivot joint 78—used to match the anatomy of the leg). The inflation of the air bladder within flexion correcting brace 104 has urged the knee into a true 0° flexion/full extension state. By selectively inflating and deflating the air bladder, the user can achieve a range of flexion states near the true 0° flexion/full extension state.

The reader will thereby appreciate that flexion correcting brace 104 can be added to an existing rehabilitation brae. Further, by adjusting the length and width of the flexion correcting brace, it can be adapted for use with a wide variety of different existing rehabilitation braces.

Figure 19:
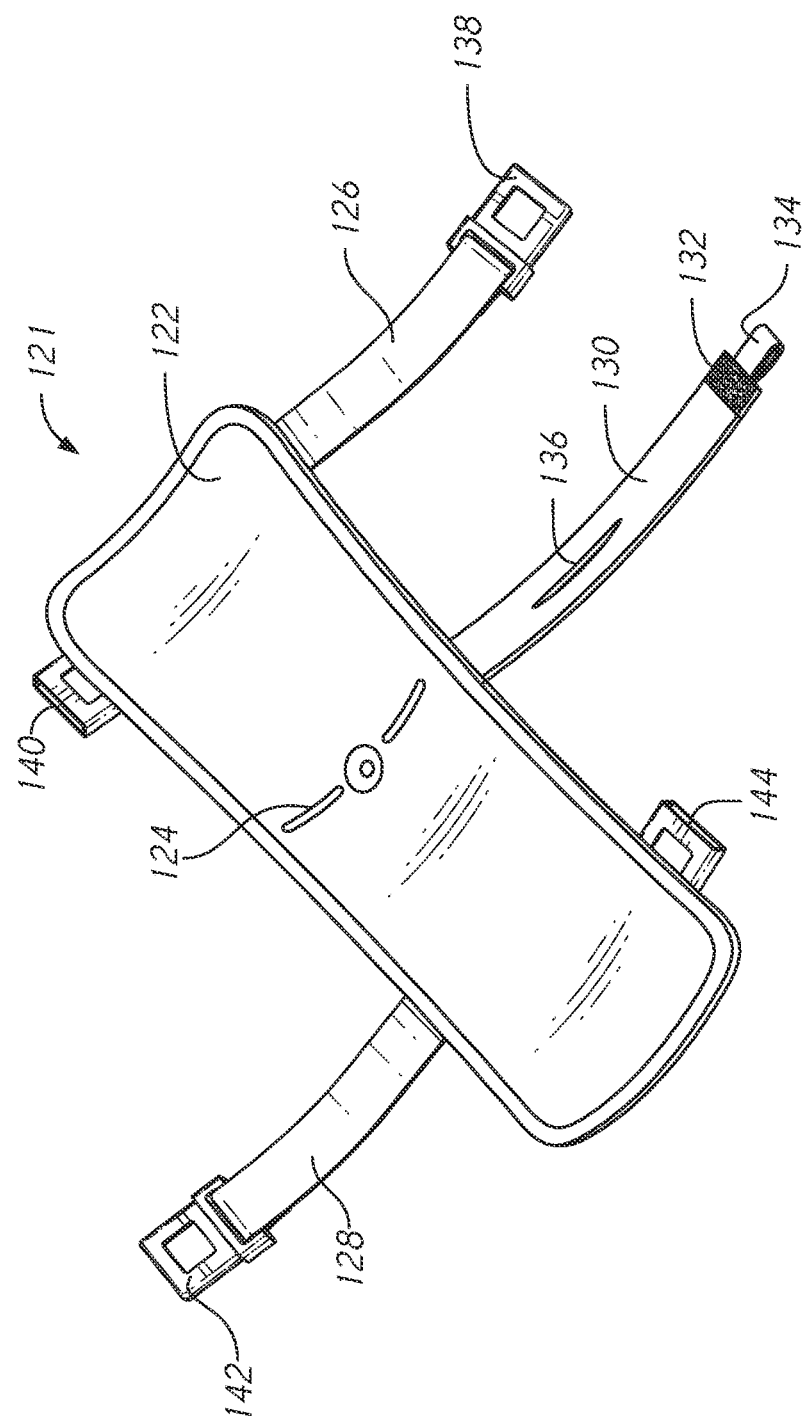
FIG. 19 is a perspective view, showing an additional embodiment of the inventive brace.

Another stand-alone embodiment of the inventive brace is depicted in FIGS. 19-23. FIG. 19 shoes a view of splint chassis 121—looking at the side configured to mate to the posterior of the knee. Pliable liner 122 is a soft and comfortable surface that may be placed against the patient's skin. Alignment marks 124 are preferably provided to assist in the initial proper placement of the splint chassis. The circle is intended to lie immediately behind the knee. The two lateral lines assist in placement—They are intended to align with the knee's pivot axis.

Thigh strap 126 and shin strap 128 are provided. These straps have male snap buckles 138, 142 that are configured to snap into female snap buckles 140,144. In the example shown, the female snap buckle for the thigh strap is positioned on the opposite side to the female snap buckle for the shin strap. From the wearer's vantage point, thigh strap 126 buckles from left to right whereas shin strap 128 buckles from right to left. The opposite buckling direction help a wearer don the splint without assistance. Each strap preferably includes length adjusting features. As an example, each end of the strap may pass around a buckle and then secure back to itself.

Knee strap 130 is provided proximate the middle of the brace. Patella slit 136 is provided in the knee strap (The function of the patella slit will be explained subsequently). Hook panel 132 is provided proximate the distal end of the knee strap. Pull tab 134 is provided so that the user can more easily grasp and pull the knee strap.

Figure 20:
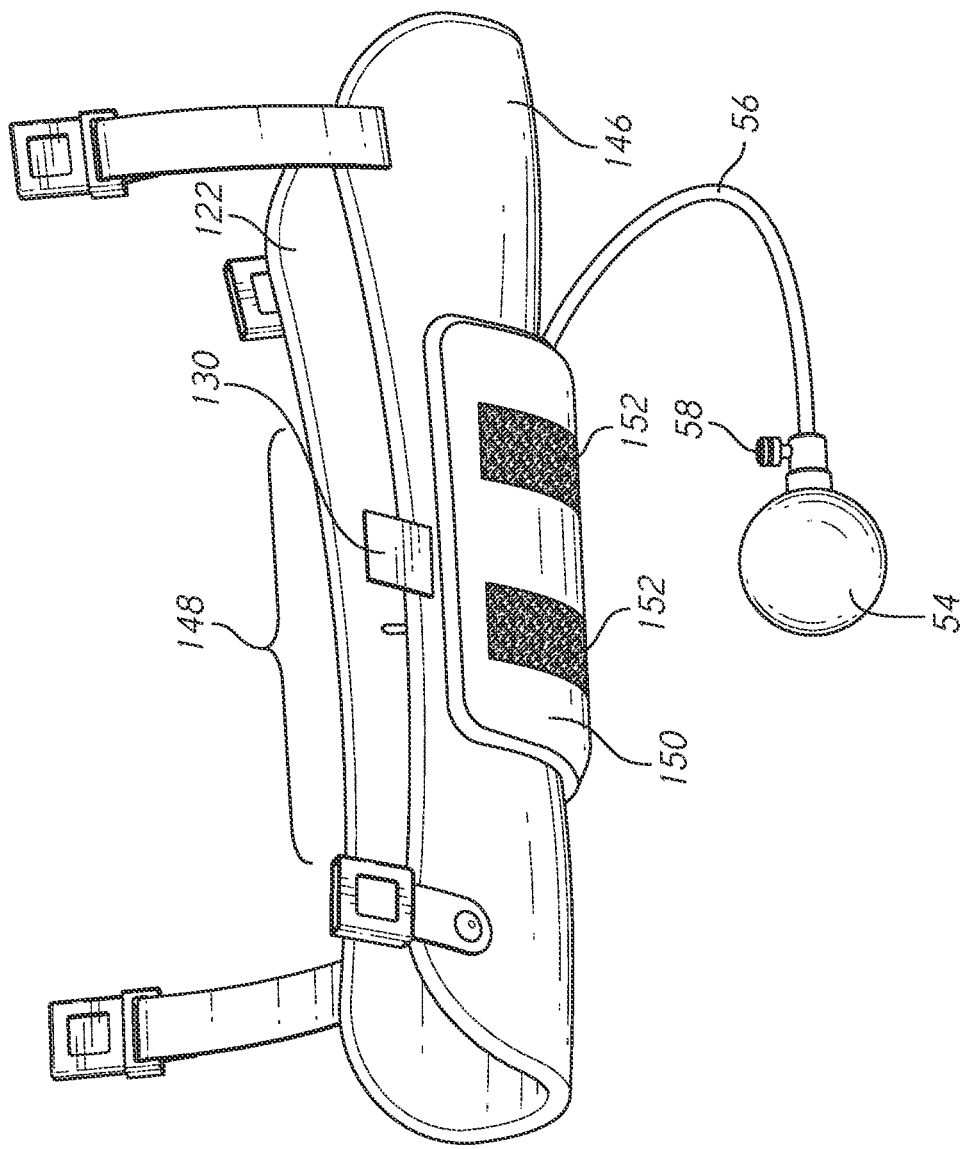
FIG. 20 is a perspective view, showing the embodiment of FIG. 19 from a different vantage point.

FIG. 20 provides an additional perspective view from a different vantage point. Rigid shell 146 contains pliable liner 122. In this example, integrated bladder 150 is attached directly to the posterior surface of rigid shell 146. The integrated air bladder does not have a separate cover. Rather, it is an expandable bladder with one surface connected to the rigid shell itself. One or more loop panels 152 are provided on the outward facing surface of the integrated bladder (The term "loop panel" encompasses any material that can be engaged by a hook panel, and is not limited to traditional VELCRO pile). As for the prior examples, squeeze bulb 54 is used to selectively inflate integrated bladder 150 through air line 56. Valve 58 is used to release pressure.

In the view of FIG. 20, knee strap 130 is cut away so that the user may more readily observe a lateral relief 148 that is provided on each side of rigid shell 146. This lateral relief is provided in the vicinity of the knee joint itself. The presence of the lateral relief allows greater potential posterior movement of the knee—as will be explained.

In the example shown, straps 126,128,130 are depicted as attaching to the exterior surface of the rigid shell 146. In other examples these straps and their corresponding female strap buckles will attach to the interior surface of the rigid shell—between the rigid shell and the pliable liner. In still other examples some of the straps will attach to the exterior of the rigid shell while others will attach to the pliable liner.

Figure 21:
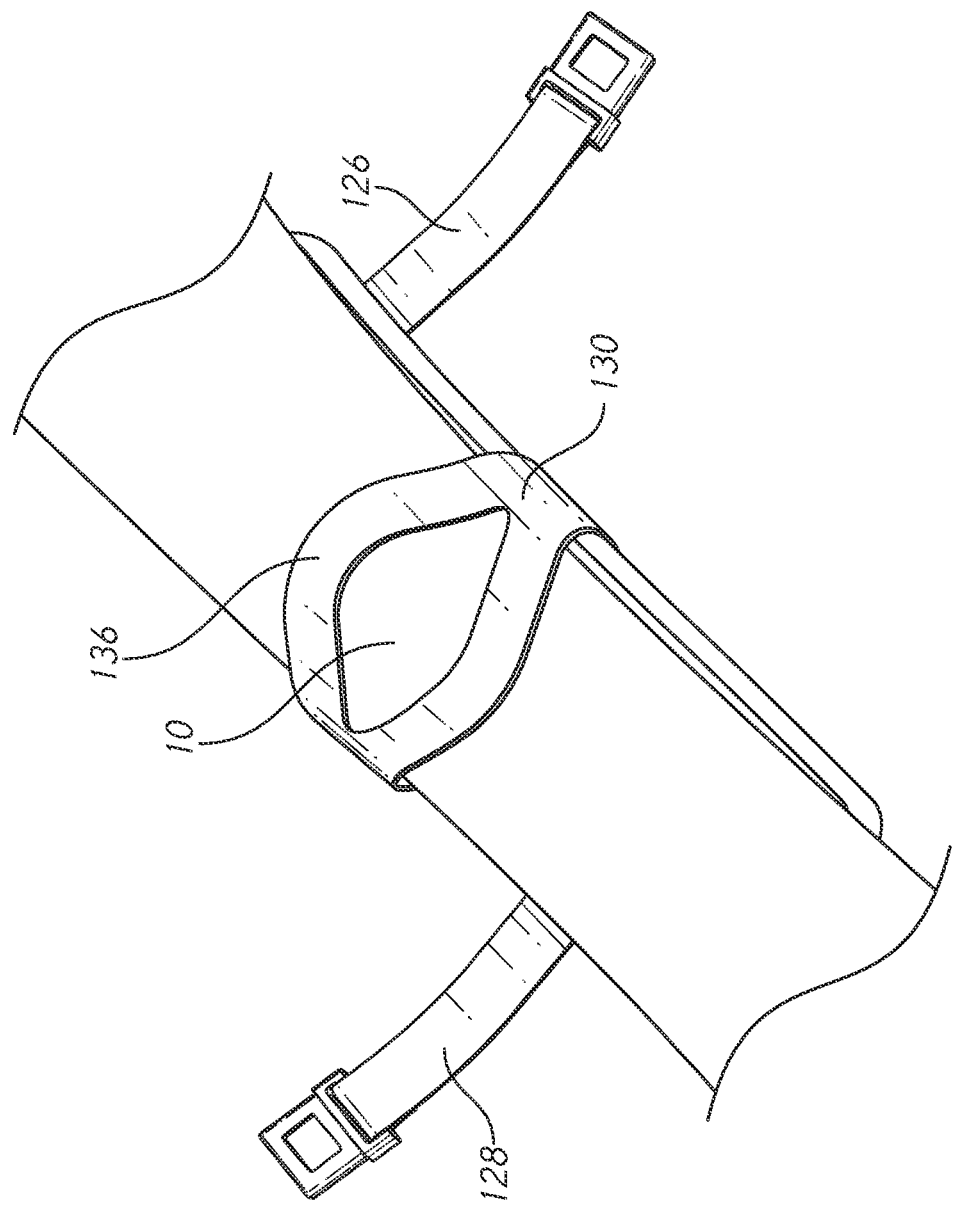
FIG. 21 is a perspective view, showing the embodiment of FIG. 19 being installed on a patient.
Figure 22:
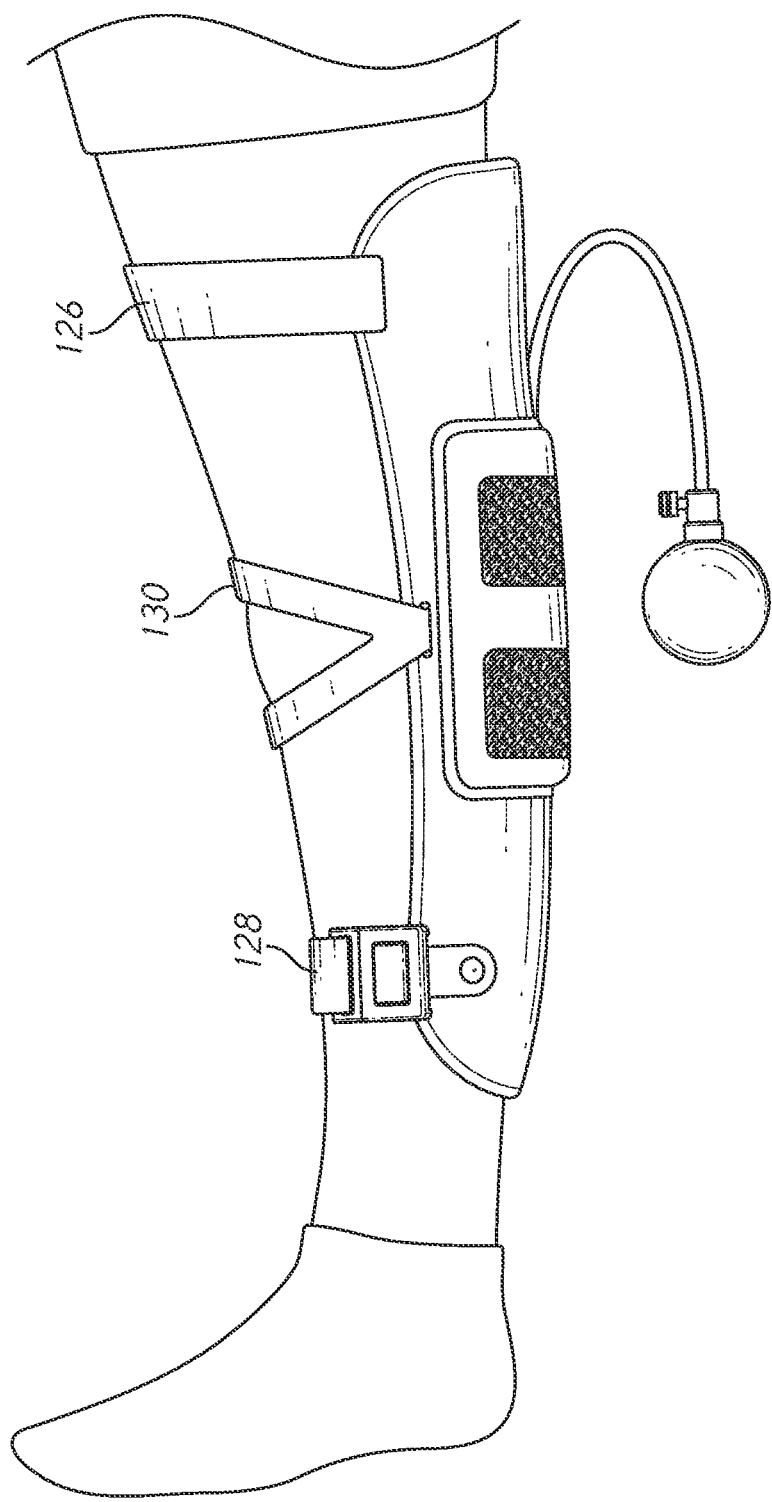
FIG. 22 is an elevation view, showing the embodiment of FIG. 19 being installed on a patient.
Figure 23:
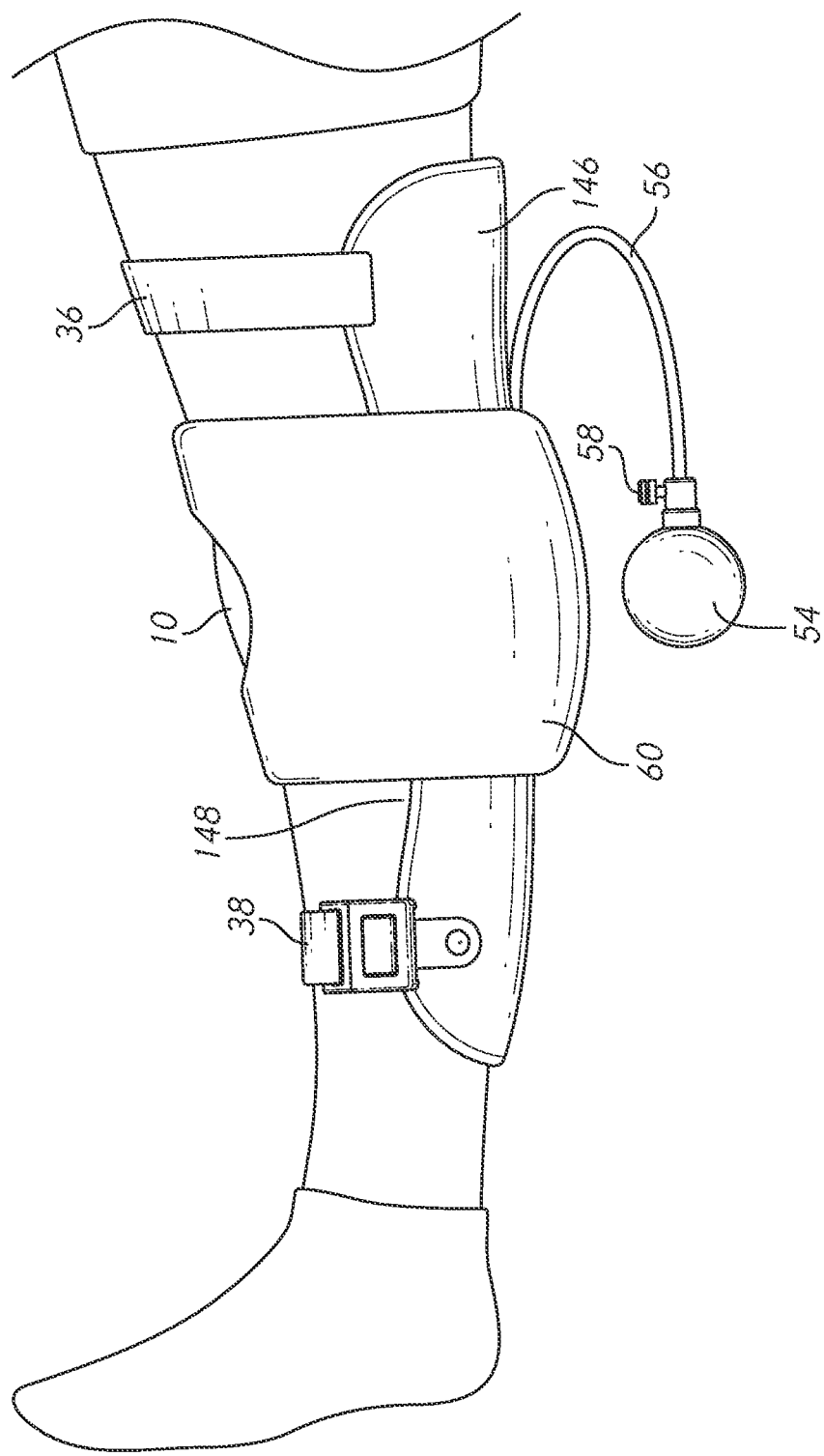
FIG. 23 is an elevation view, showing the embodiment of FIG. 19 being installed on a patient.

FIGS. 21-23 show the process of installing and activating this embodiment. In FIG. 21, the splint chassis has been scoured in position on the back of the knee by passing knee strap 130 around the knee and securing the hook panel on the knee strap to a loop panel 152 on a lateral or posterior surface of the splint assembly (such as a loop panel 152). The reader will note how patella slit 136 has been opened so that a portion of the knee strap passes above knee 10 and a portion passes below it. The knee strap is preferably made of an elastic material so that the user can grasp the pull tab on the end of the knee strap and pull it into a stretched state before securing the patella slit over the knee. Once secured as shown, the knee strap holds the entire splint assembly in place. This allows the user to secure the other components of the invention in a methodical manner, without having to worry about maintaining the position of the splint assembly.

FIG. 22 provides a side elevation view of the splint assembly installed on a patient's knee. Knee strap 130 secures the assembly in place while the user (or another person) secures and adjusts thigh strap 126 and shin strap 128.

In FIG. 23, knee wrap 60 has been passed around knee 10 and secured (as for the embodiment of FIG. 11). Squeeze bulb 54 is then operated to inflate the integrated bladder 150. This inflation moves the knee joint in the posterior direction and reduces the flexion angle by a desired amount.

Lateral relief 148 provides clearance for knee wrap 60—even when the patient has a small knee circumference. FIG. 23 shows a patient having a fairly large knee. In this instance the inflation of the air bladder and consequent posterior movement of knee wrap 60 can provide proper flexion adjustment without the presence of the lateral relief. However, for a slim patient, the presence of lateral relief 148 provides a significant advantage. Absent the lateral relief, the lateral sides of rigid shell 146 can inhibit knee wrap 60's ability to urge the knee further into the rigid shell (and thereby inhibit the attainment of a true 0° flexion/full extension state).

Figure 24:
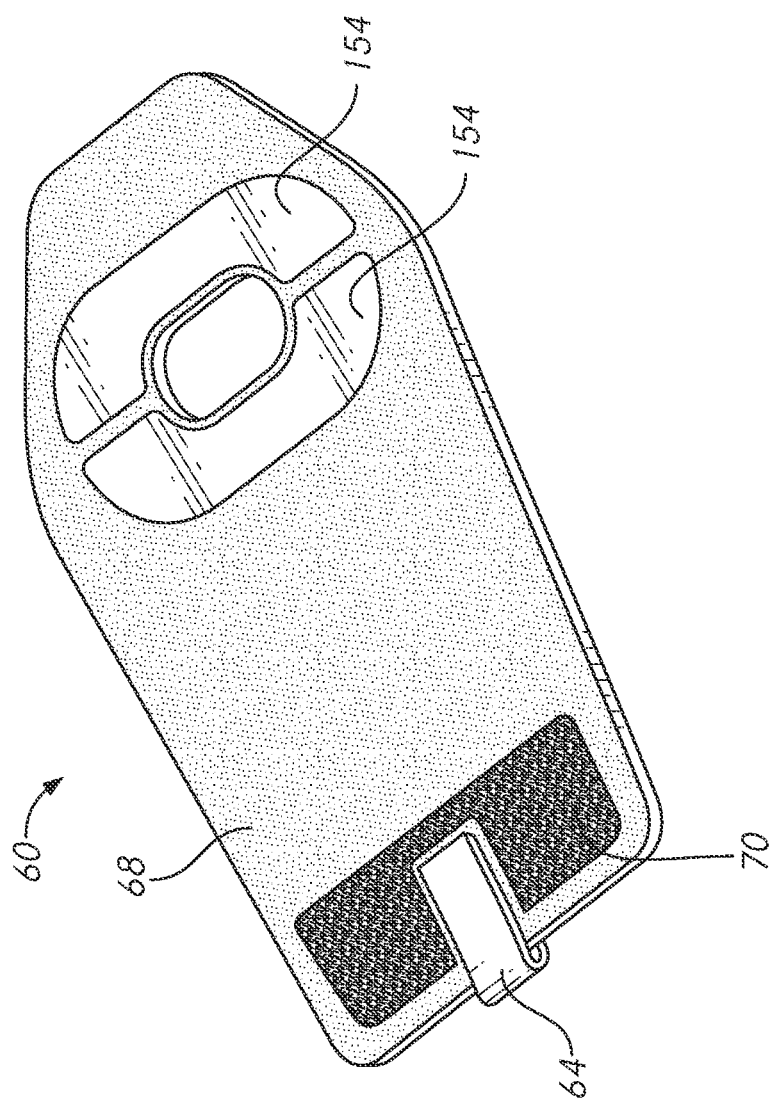
FIG. 24 is a perspective view, showing cold packs being added to the knee wrap.

The present invention can be used in conjunction with other therapies. One good example is the addition of cold therapy. Cold therapy is often used to limit post-operative or post-rehabilitation swelling in the knee joint. FIG. 24 shows a view of the interior surface 68 of knee wrap 60 (the side that faces the patient). This interior surface is covered in loop material (defined again as any material that can be engaged by a hook panel). One or more cold packs 154 are provided. Each of these cold packs has one or more hook panels on the side facing away from the viewer in FIG. 24. The user can place each cold pack in any desired location. By pressing the cold pack against interior surface 68, the hook panel(s) on the cold pack engages the interior surface of the knee wrap and holds the cold pack in position. The version of the cold pack shown includes a knee relief to avoid contact with the patient's patella.

The cold packs can be simple water-filled bags or gel-filled bags. Preferably, however, each cold pack has a more sophisticated thermal transfer media that freezes into a substance resembling snow. This allows the bag to be malleable so that it can conform to the patient's anatomy. The heat transfer media in the cold packs is preferably a hydrating liquid consisting of a solution of water and a humectant selected from the group consisting of propylene glycol, ethylene glycol, glycerin, dimethyl sulfoxide, dimethyl formamide, and combinations thereof. The thermal capacitance of each heat transfer pack can be increased by adding smaller sub-bags of pure water. These will freeze solid, but they are small enough that the overall bag itself remains malleable.

Once the user places fresh cold packs as shown in FIG. 24, the user secures knee wrap 60 around the knee as shown in FIG. 23. The knee wrap presses the cold packs, against the patient's knee. Further, by activating squeeze bulb 54, even more pressure is added to press the cold packs against the knee. The presence of lateral reliefs 148 provide additional space for the addition of the cold packs. The reliefs allow the use of a wider cold pack.

Those skilled in the art will know that some existing systems use cooling bladders with a separate pump that circulates a cooling fluid through the cooling bladder. Such a cooling bladder can be used in the present invention. A cooling bladder is placed in the position of the cold packs in FIG. 24. The cooling bladder has hook panels so that it can be attached to the wrap in any desired position. A circulation pump forces a cool fluid through this bladder.

Still looking at FIG. 24, the reader will note that pull tab 64 is made as a loop. The pull tab is preferably made of an elastic material. Once the entire assembly is in place (as shown in FIG. 23) and the pressure of the air bladder is set as desired, the user can tuck squeeze bulb 54 into the loop of pull tab 64. The pull tab will retain the squeeze bulb until it is needed again.

It is also possible to apply cold packs to the embodiment of FIG. 15. If cold packs are desired, the inward facing surface of inflatable bladder 120 can be covered in loop material. The cold packs can be secured to this loop material using the hook tab(s) on each cold pack.

In general the inflatable air bladder should be located within the circumference of the knee wrap when it is installed around the patient's knee. The location of the air bladder should be selected so that it urges the knee joint in the posterior direction when it is inflated. In the embodiment of FIG. 8 and the embodiment of FIG. 23 the air bladder is located on the convex outer surface of the rigid shell. When the air bladder is located in this position, increasing pressure causes an increase in tension in the knee wrap—which urges the knee joint in the posterior direction.

Figure 25:
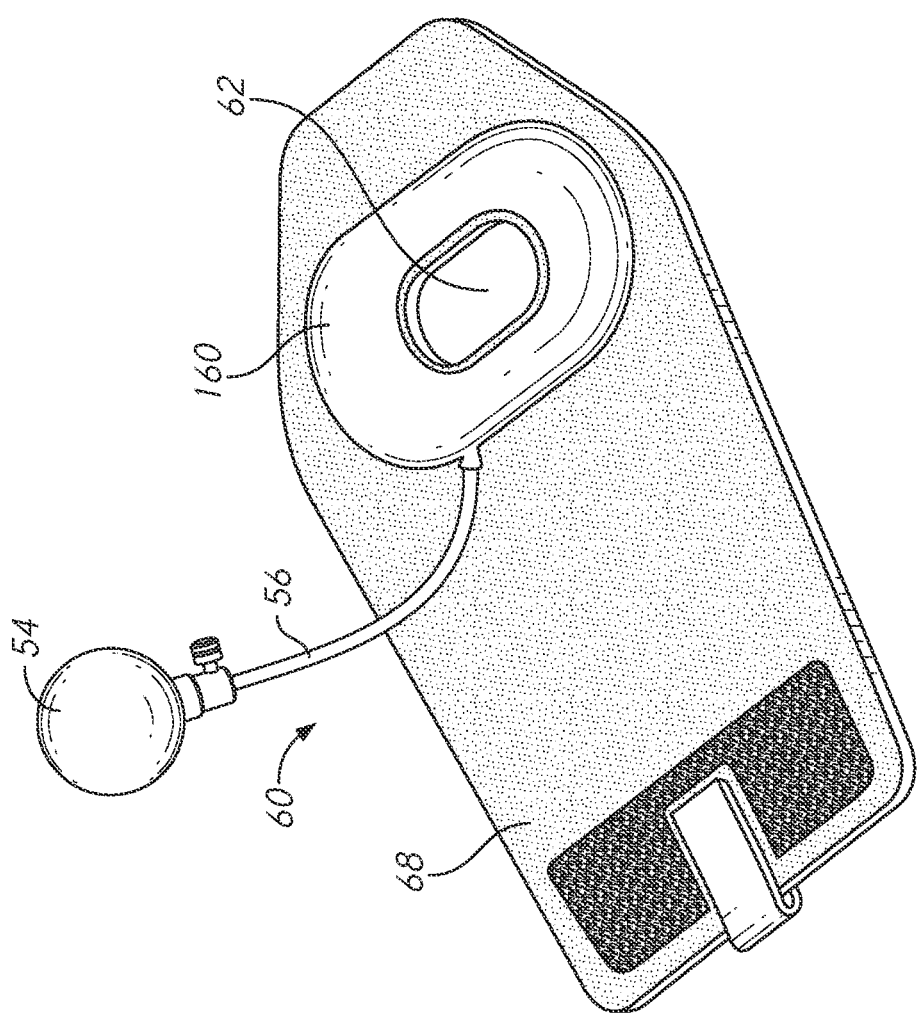
FIG. 25 is a perspective view, showing an alternate location for the inflatable air bladder.
Figure 26:
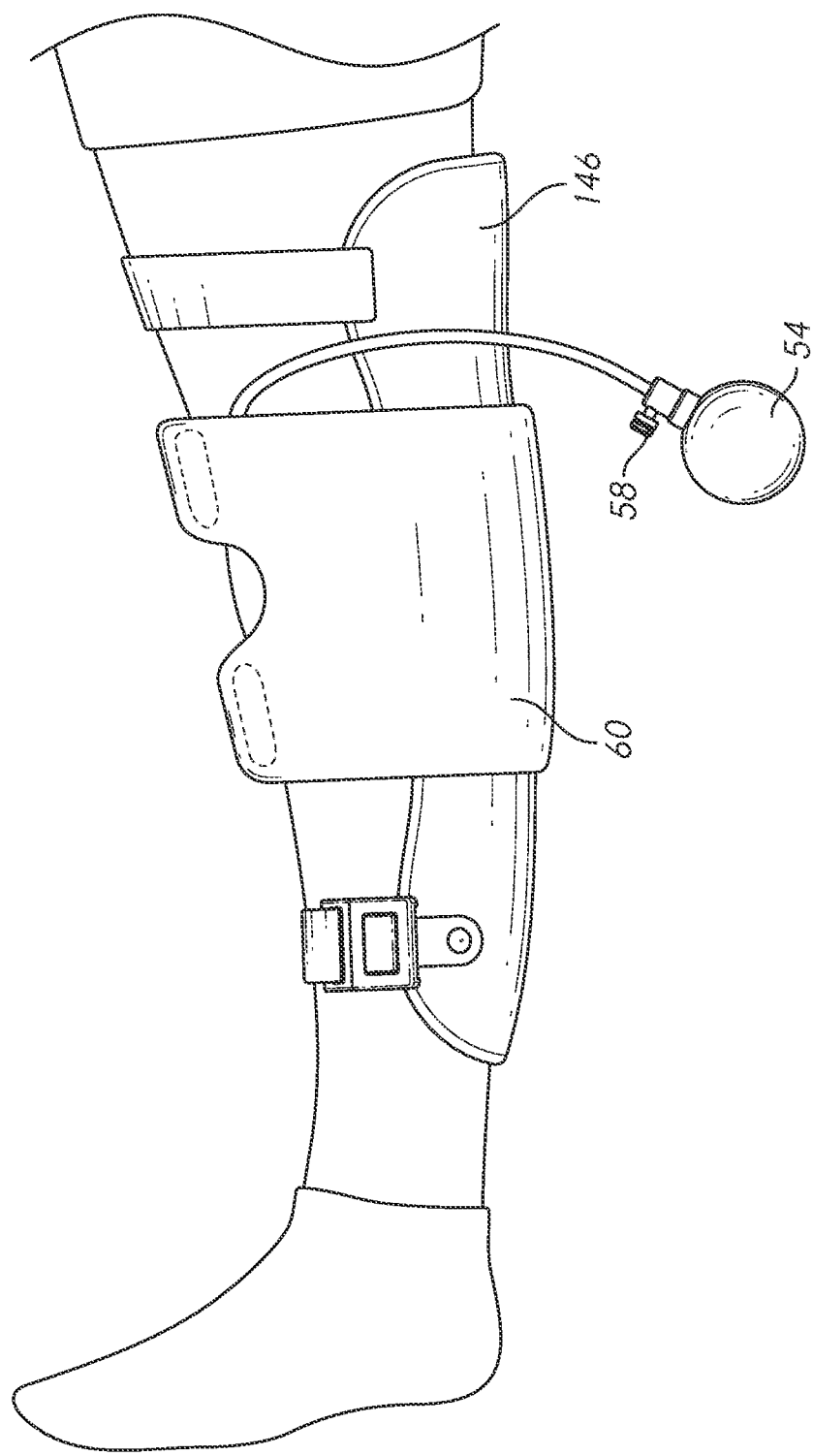
FIG. 26 is an elevation view, showing the embodiment of FIG. 25 in operation.

It is also possible to locate the air bladder on the anterior side of the knee joint while still keeping the air bladder within the circumference of the knee wrap. FIGS. 25 and 26 shown am embodiment of this configuration. In FIG. 25, air bladder 160 is provided on interior surface 68 of knee wrap 60. The air bladder surrounds knee cap relief 62. Squeeze bulb 54 provides selective inflation of the air bladder as for the prior examples.

FIG. 26 shows this embodiment in an installed state. The reader will observe how the inflation of the air bladder urges the knee joint in the posterior direction.

The invention has many other features that can be used individually or combined in various ways. These include:

1. An initial pressure can be established to create an initial flexion angle. The treater can then increase the pressure over time to decrease the flexion angle as desired.

2. The treater can adjust the pressure in a cyclic fashion to create periods of stretching and periods of relaxation.

3. The pressure can be released in order to change expended cold packs for fresh cold packs, and then reapplied.

4. In the case of a rehabilitative brace, the pressure can be applied when the knee is immobile and not undergoing rehab exercises.

5. The inflatable air bladder could be inflated using a battery-powered pump. Automatic pressure settings could be provided as well.

6. Muscle stimulation therapy, as governed by an electrical stimulation device that is included with the inventive brace or attached to the inventive brace.

7. The addition of a 1 to 2 cm pad in the region of the posterior tibia to offload posterior cruciate ligament reconstruction. The brace's soft liner is preferably provided with VELCRO-compatible material, so that additional and customizable pads can be added where desired.

8. Heat packs can be substituted for the cold packs described previously. Alternatively, resistive heating elements could be belt into the inventive brace (such as within the knee wrap).

Although the preceding descriptions present considerable detail they should be properly viewed as illustrating embodiments of the present invention rather than limiting the scope of the invention. Many more embodiments following the same principles will occur to those skilled in the art. Accordingly, the cope of the invention should be fixed by the following claims rather than by the examples given.

Having described our invention, we claim:

1. A flexion limiting knee brace configured to adjust and maintain a desired amount of flexion in a human knee joint of a human leg, comprising:
   (a) a rigid shell, having a concave inner surface and a convex outer surface;
   (b) a pliable liner proximate said concave inner surface of said rigid shell;
   (c) a knee wrap configured to secure around said human knee joint and said rigid shell when said rigid shell is placed along a posterior side of said human leg;

(d) an inflatable bladder contained within a circumference of said knee wrap when said knee wrap is secured around said human knee joint and said rigid shell is placed along a posterior side of said human leg, said inflatable bladder being configured to urge said human knee joint in a posterior direction when inflated in order to put said human knee joint in 0° flexion state; and (e) a pump for inflating said inflatable bladder.

2. A flexion limiting knee brace as recited in claim 1, wherein said inflatable bladder is located on said convex outer surface of said rigid shell.

3. A flexion limiting knee brace as recited in claim 2, wherein:
   (a) said knee wrap has an interior surface and an exterior surface;
   (b) said exterior surface of said knee wrap includes hook-compatible material;
   (c) said interior surface of said knee wrap includes a knee wrap hook panel.

4. A flexion limiting knee brace as recited in claim 3, comprising
   (a) said inflatable bladder includes hook-compatible material;
   (b) a knee strap having a first end and a second end;
   (c) said first end of said knee strap being attached to a first side of said knee brace; and
   (d) said second end of said knee strap having a knee strap hook panel configured to engage said hook-compatible material on said inflatable bladder.

5. A flexion limiting knee brace as recited in claim 4, wherein said knee strap includes a patella slit.

6. A flexion limiting knee brace as recited in claim 5, wherein said knee strap is made of elastic material.

7. A flexion limiting knee brace as recited in claim 1, wherein:
   (a) said knee wrap has an interior surface and an exterior surface;
   (b) said exterior surface of said knee wrap includes hook-compatible material;
   (c) said interior surface of said knee wrap includes a knee wrap hook panel.

8. A flexion limiting knee brace as recited in claim 1, wherein said pump comprises a squeeze bulb.

9. A flexion limiting knee brace as recited in claim 1, comprising a cold pack including a hook panel configured to engage said hook-compatible material on said interior surface of said knee wrap, thereby affixing said cold pack to said interior surface of said knee wrap.

10. A flexion limiting knee brace as recited in claim 1, wherein said inflatable bladder is attached to said knee wrap.

11. A flexion limiting knee brace configured to adjust and maintain a desired amount of flexion in a human knee joint of a human leg, comprising:
    (a) a shell, having a concave inner surface and a convex outer surface, with a soft liner attached to said shell;
    (b) a knee wrap configured to encircle said human knee joint and said shell when said shell is placed along a posterior side of said human leg;
    (c) an inflatable bladder contained within a circumference of said knee wrap when said knee wrap is secured around said human knee joint with said shell placed along a posterior side of said human leg;
    (d) wherein said inflatable bladder is positioned to urge said human knee joint in a posterior direction when inflated in order to put said human knee joint in 0° flexion state; and
    (e) a pump for inflating said inflatable bladder.

12. A flexion limiting knee brace as recited in claim 11, wherein said inflatable bladder is located on said convex outer surface of said shell.

13. A flexion limiting knee brace as recited in claim 12, wherein:
    (a) said knee wrap has an interior surface and an exterior surface;
    (b) said exterior surface of said knee wrap includes hook-compatible material;
    (c) said interior surface of said knee wrap includes a knee wrap hook panel.

14. A flexion limiting knee brace as recited in claim 13, comprising:
    (a) said inflatable bladder includes hook-compatible material;
    (b) a knee strap having a first end and a second end;
    (c) said first end of said knee strap being attached to a first side of said knee brace; and
    (d) said second end of said knee strap having a knee strap hook panel configured to engage said hook-compatible material on said inflatable bladder.

15. A flexion limiting knee brace as recited in claim 14, wherein said knee strap includes a patella slit.

16. A flexion limiting knee brace as recited in claim 15, wherein said knee strap is made of elastic material.

17. A flexion limiting knee brace as recited in claim 11, wherein:
    (a) said knee wrap has an interior surface and an exterior surface;
    (b) said exterior surface of said knee wrap includes hook-compatible material;
    (c) said interior surface of said knee wrap includes a knee wrap hook panel.

18. A flexion limiting knee brace as recited in claim 11, wherein said pump comprises a squeeze bulb.

19. A flexion limiting knee brace as recited in claim 11, comprising a cold pack including a hook panel configured to engage said hook-compatible material on said interior surface of said knee wrap, thereby affixing said cold pack to said interior surface of said knee wrap.

20. A flexion limiting knee brace as recited in claim 11, wherein said inflatable bladder is attached to said knee wrap.

* * * * *